(12) United States Patent
Krespi et al.

(10) Patent No.: US 9,943,305 B2
(45) Date of Patent: Apr. 17, 2018

(54) SURGICAL PROCEDURE AND RELATED APPARATUS FOR TREATING SLEEP APNEA BY LIFTING, SUSPENDING AND STIFFENING THE SOFT PALATE

(71) Applicant: Snorx, LLC, New York, NY (US)

(72) Inventors: Yosef P. Krespi, New York, NY (US); David Volpi, New York, NY (US)

(73) Assignee: Zelegent, Inc., Irvine, CA (US)

( * ) Notice: Subject to any disclaimer, the term of this patent is extended or adjusted under 35 U.S.C. 154(b) by 298 days.

(21) Appl. No.: 14/494,278

(22) Filed: Sep. 23, 2014

(65) Prior Publication Data

US 2015/0088166 A1 Mar. 26, 2015

Related U.S. Application Data

(60) Provisional application No. 61/883,009, filed on Sep. 26, 2013.

(51) Int. Cl.
*A61B 17/04* (2006.01)
*A61F 5/56* (2006.01)
*A61B 17/00* (2006.01)
*A61B 17/06* (2006.01)

(52) U.S. Cl.
CPC ...... *A61B 17/0467* (2013.01); *A61B 17/0482* (2013.01); *A61B 17/0483* (2013.01); *A61B 17/06109* (2013.01); *A61B 17/06166* (2013.01); *A61F 5/566* (2013.01); *A61B 17/06004* (2013.01); *A61B 2017/00004* (2013.01); *A61B 2017/06042* (2013.01); *A61B 2017/06052* (2013.01); *A61B 2017/06176* (2013.01)

(58) Field of Classification Search
CPC ...... A61B 17/0467; A61B 2017/06176; A61B 2017/06052; A61F 5/566
See application file for complete search history.

(56) References Cited

U.S. PATENT DOCUMENTS

| | | | | |
|---|---|---|---|---|
| 6,110,183 | A * | 8/2000 | Cope | A61B 17/0401 606/139 |
| 2008/0066766 | A1* | 3/2008 | Paraschac | A61F 5/566 128/848 |
| 2010/0137679 | A1* | 6/2010 | Lashinski | A61B 17/0401 600/37 |
| 2011/0245850 | A1* | 10/2011 | van der Burg | A61B 17/0401 606/145 |
| 2013/0144337 | A1* | 6/2013 | Stone | A61B 17/0401 606/232 |
| 2013/0172931 | A1* | 7/2013 | Gross | A61F 5/566 606/230 |

* cited by examiner

Primary Examiner — Thomas McEvoy
(74) Attorney, Agent, or Firm — K&L Gates LLP

(57) ABSTRACT

Methods and apparatuses for lifting, suspending and stiffening a patient's tissue are disclosed. In an embodiment, a method of lifting and stiffening a patient's tissue includes inserting at least one suture into the patient's tissue in a first direction, pulling the suture in a second direction so as to lift and suspend the tissue in a lifted position and stiffen the tissue in the lifted position, and cutting the suture so that the tissue remains in the lifted position. Preferably, the patient's tissue is the patient's soft palate.

13 Claims, 38 Drawing Sheets

The Ikematsu System for the
Diagnosis of Snoring

Natural type

Elongated uvula

Enlarge uvula

Parallel type

Webbed type

Large tongue dorsum

Tonsillar hypertrophy

Shallow

Posterior arch narrowing

Bifid Uvula

Imbedded type

Emerging type Anterior arch narrowing palate pharyngeal folds

SURGICAL PROCEDURE AND RELATED APPARATUS FOR TREATING SLEEP APNEA BY LIFTING, SUSPENDING AND STIFFENING THE SOFT PALATE

CROSS REFERENCE TO RELATED APPLICATIONS

This application claims the benefit of U.S. provisional patent application No. 61/883,009, filed Sep. 26, 2013, the entire disclosure of which is incorporated herein by reference.

FIELD OF THE INVENTION

The present disclosure relates generally to methods and apparatuses for lifting, suspending and stiffening a patient's tissue, and more specifically to treating sleep apnea by lifting, suspending and stiffening a patient's soft palate and/or uvula.

BACKGROUND

Snoring affects approximately 50% of men and 30% of women and is commonly caused by the oscillation of the uvula, the free edges of the soft palate (also known as the velum or muscular plate) and the faucial pillars. Chronic snorers often report restless sleep, morning headaches and excessive fatigue. Other common findings are memory and concentration difficulties, behavioral changes including irritability, impotence and loss of alertness, and even sudden death from accidents or cardiovascular complications.

Snoring is a precursor to obstructive sleep apnea syndrome (OSA), and can be a risk factor for hypertension, cardiac arrhythmias, angina pectoris, cerebral infarction, pulmonary hypertension and congestive heart failure, all of which are commonly associated with OSA. OSA is the most common type of sleep apnea and results from the collapse of the pharyngeal wall in response to negative inspiratory pressure in the upper airway. Hypotonicity of the pharyngeal musculature allows the upper airway to collapse even at the most modest negative inspiratory pressures, leading to snoring or apnea. The collapse occurs when the negative pressure within the pharynx exceeds the ability of its walls and musculature to maintain a patient airway. Any narrowing along the upper airway will increase the pressure and subsequently promote further narrowing or will require an increase in the velocity of airflow, further reducing intraluminal pressure.

A redundant palate or elongated or thick uvula can also cause snoring from the rapid airflow created by inspiratory pressure. Further anatomic narrowing or obstruction anywhere along the upper airway can cause OSA. Other causes of physiologic dysfunction of neuromuscular and respiratory control mechanisms can also cause OSA.

Various methods have been developed to treat snoring and OSA. Uvulopalatopharyngoplasty (UPPP) was first designed as a surgical treatment for snoring and was later applied to OSA. UPPP is performed by removing the anterior surface of the soft palate and uvula and suturing the uvula to the soft palate. There are, however, risks associated with UPPP such as causing excess scar tissue to tighten the airway and actually making the airway smaller than before UPPP.

Laser assisted uvulopalatoplasty (LAUP) was developed as an alternative to UPPP to treat OSA. LAUP is performed by using a laser, typically a $CO_2$ laser, to remove parts of the uvula. LAUP also has its risks, as the scar tissue from the laser can reduce the airspace in the pharynx, leading to velopharyngeal insufficiency. The scar tissue can also make the airway more prone to collapse during sleep.

Several other procedures have also been developed to treat OSA. For example, somnoplasty uses radiofrequncy ablation to cause coagulation necrosis (clotting) in the tissue in a patient's mouth. Pillar implants can be inserted into a patient's soft palate to cause the palate to stiffen. Sclerotherapy uses a medicinal injection to shrink blood vessels. Each of these alterative procedures also has associated disadvantages. For example, these alternative procedures do not allow a doctor to lift and suspend the soft palate. These procedures are also permanent, that is, once the tissue is removed, it cannot be replaced.

SUMMARY

The present disclosure provides methods and apparatuses for lifting, suspending and stiffening a patient's tissue, specifically a patient's soft palate and/or uvula. In an example embodiment, a method of lifting and stiffening a patient's tissue includes inserting at least one suture into the patient's tissue in a first direction, pulling the suture in a second direction so as to lift and suspend the tissue in a lifted position and stiffen the tissue in the lifted position, and cutting the suture so that the tissue remains in the lifted position.

In another example embodiment, a method of lifting and stiffening a patient's tissue includes loading a suture onto a piercing shaft of a suture insertion device, inserting the piercing shaft into the patient's tissue in a first direction, releasing the suture from the piercing shaft, withdrawing the piercing shaft from the patient's tissue, and pulling the suture in a second direction so as to lift, suspend and stiffen the tissue.

In another example embodiment, a suture insertion device, includes a body and a piercing shaft connected to the body, the piercing shaft including a piercing end, the piercing shaft configured to pierce a patient's tissue with the piercing end and insert a suture into the patient's tissue in a first direction, wherein the piercing shaft is further configured to release the suture into the patient's tissue such that the suture can be pulled in a second direction to lift, suspend and stiffen the patient's tissue once the piercing shaft is removed from the patient's tissue.

In another example embodiment, a suture insertion device, includes a means for loading a suture, a means for inserting the suture into a patient's tissue in a first direction, and a means for releasing the suture so that the suture can be pulled in a second direction different from the first direction so as to lift, suspend and stiffen the tissue.

In another example embodiment, a suture insertion device includes a body, a piercing shaft connected to the body, the piercing shaft including a cannula and a threading notch configured to receive a suture, and an insertion shaft moveable within the cannula, the insertion shaft configured to release the suture from the piercing shaft.

In another example embodiment, a suture insertion device includes a body, a piercing shaft connected to the body, the piercing shaft including a threading notch configured to receive a suture, and a clamp configured to clamp the suture to the body when the piercing shaft is inserted into a patient's tissue and to release the suture from the body when the piercing shaft is withdrawn from the patient's tissue.

BRIEF DESCRIPTION OF THE FIGURES

Embodiments of the present disclosure will now be explained in further detail by way of example only with reference to the accompanying figures, in which.

DETAILED DESCRIPTION

Figure 1:
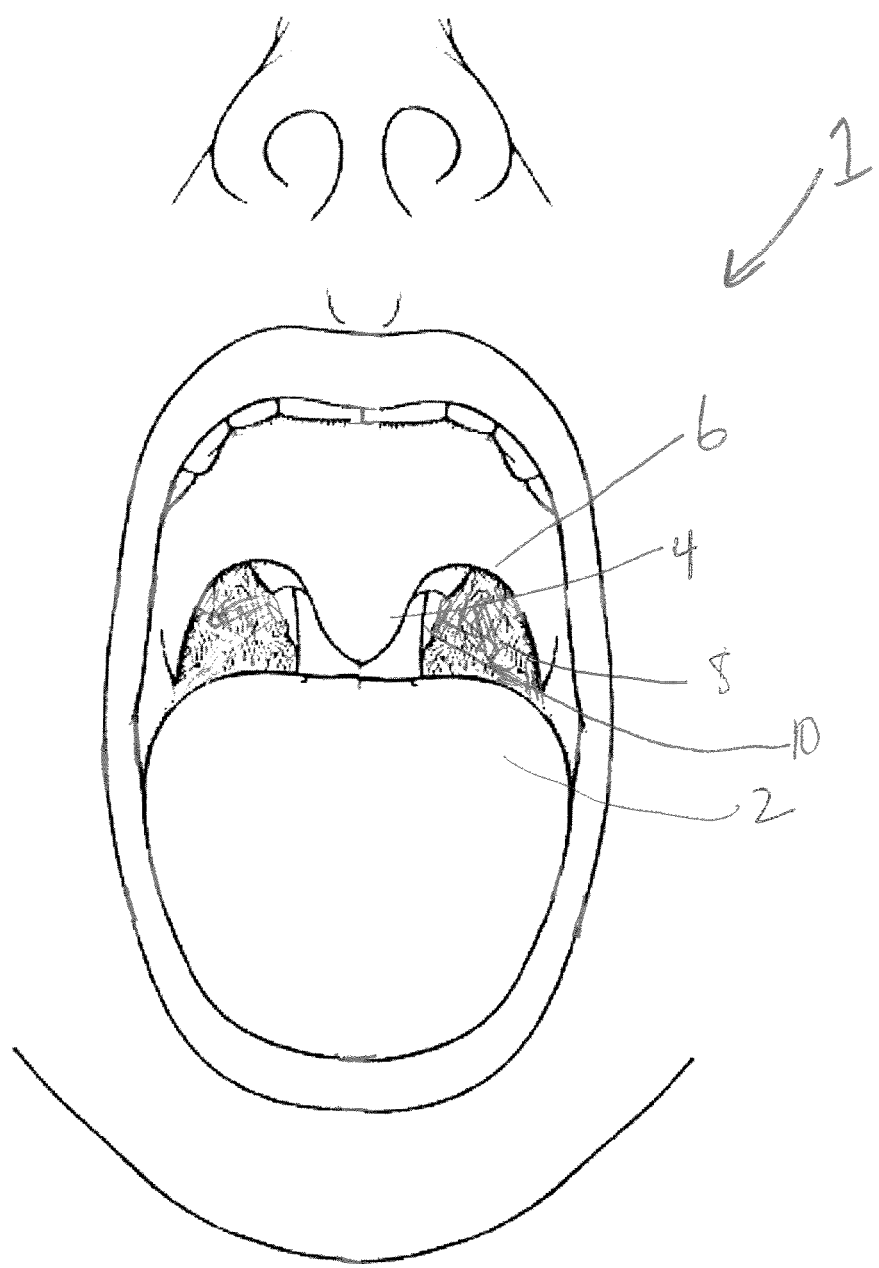
FIG. 1 is a front view of an example mouth of a snoring patient.
Figure 2:
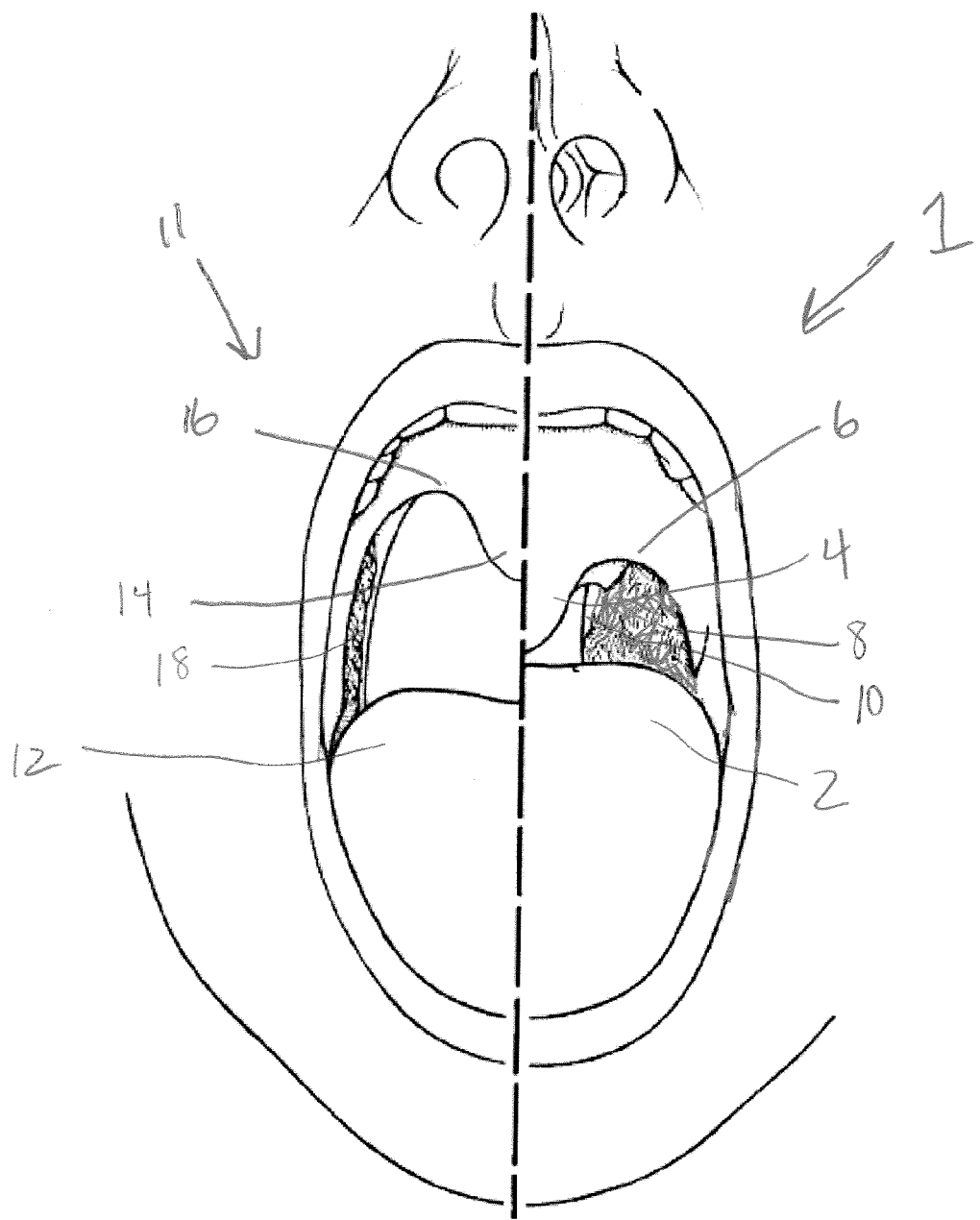
FIG. 2 is a front view comparing an example mouth of a non-snoring patient to the mouth of FIG. 1.

FIG. 1 illustrates an example mouth 1 of a typical snoring patient. FIG. 2 compares the mouth 1 of the snoring patient in FIG. 1 to an example mouth 11 of a non-snoring patient. The snoring patient's mouth 1 has a higher tongue base 2, an enlarged uvula 4, a long, low, thick palate 6, a large tonsil 8 and a vertical pharyngeal fold 10. In comparison, the non-snoring patient's mouth 11 has a lower tongue base 12, a smaller, higher uvula 14, a high, thin palate 16, a small tonsil 18 and no vertical pharyngeal fold. These differences between the snorer's mouth 1 and the non-snorer's mouth 11 can cause the snorer's upper airway to become obstructed.

The present disclosure seeks to correct at least the large uvula 4 and/or the thick palate 6 of the snoring patient's mouth 1 by providing a method and apparatus for an office-based treatment of a patient's soft palate and/or uvula to correct sleep apnea as well as symptomatic, habitual and social snoring due to palatial flutter. In an example embodiment, a method of lifting, suspending and stiffening a patient's soft palate includes inserting one or more barbed sutures into the patient's soft palate to suspend and stiffen the soft palate. The patient's soft palate can be lifted, suspended and stiffened by pulling the soft palate and/or uvula in a direction different from the insertion direction of the suture and suspending the soft palate and/or uvula in that position.

Figure 3:
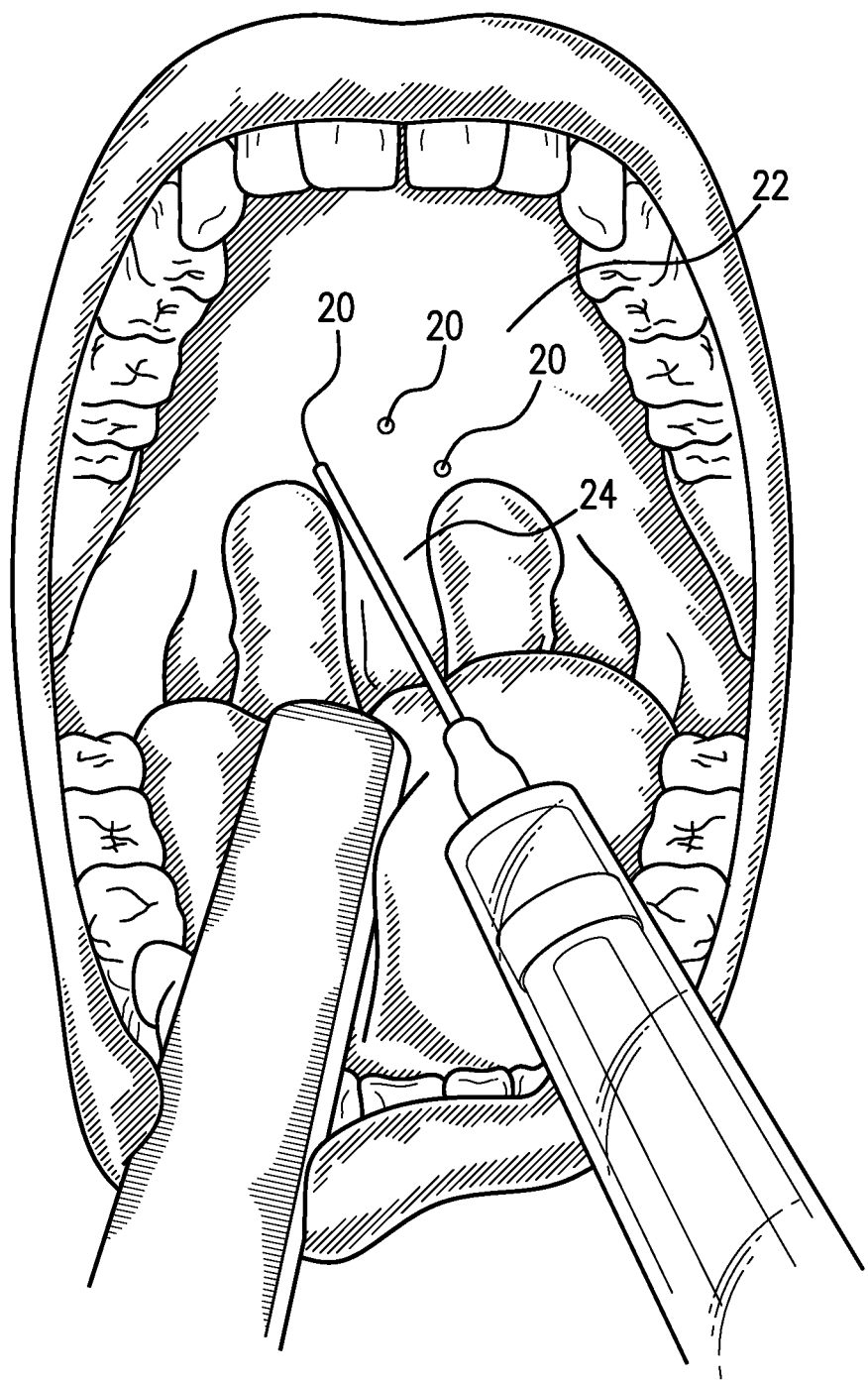
FIG. 3 is a front view of an example mouth of a snoring patient.

In an example embodiment, the present method begins by applying a local anesthesia to a patient's soft palate. Preferably, 2 cubic centimeters of 2% lidocaine with 1:100,000 epinephrine is injected at three different points 20 in the patient's soft palate 22, above the uvula 24 and near the location where one or more sutures will be inserted into the soft palate, as shown in FIG. 3. The injection should be slow and intramuscular and can take effect within minutes.

Figure 4:
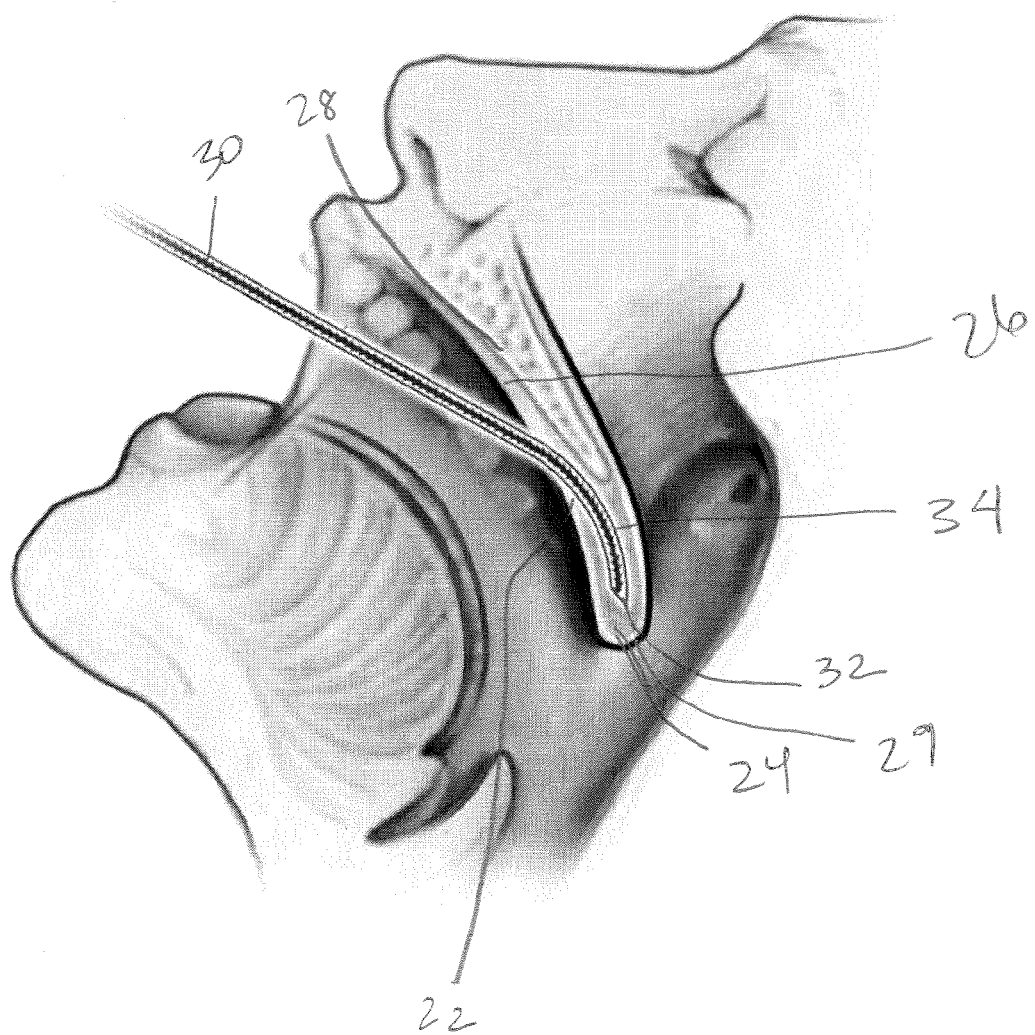
FIG. 4 is a side view illustrating an example method according to the present disclosure.

Once the patient has been anesthetized, one or more sutures can be inserted into the patient's soft palate 22 by locating the midline 26 between the patient's hard palate 28 and soft palate 22 and inserting the one or more sutures 36 into the patient's soft palate as close to the junction of the soft 22 and hard 28 palates as possible. The sutures 36 can be inserted using a needle 30 or another suture insertion device, such as the suture insertion devices described in more detail below. In an example embodiment, the sutures 36 are inserted with a needle 30 by inserting the needle 30 into the patient's soft palate 22 so that the needle 30 extends into the soft palate 22 and optionally also into the uvula 24. As illustrated in FIG. 4, the needle can be inserted into the soft palate 22 so that the piercing end 32 of the needle 30 extends to almost the tip 29 of the uvula 24. The needle 30 can optionally include depth markings so that the doctor performing the procedure can accurately determine how far the suture 36 has been inserted into the patient's soft palate 24. The needle 30 preferably includes a curved piercing end 34 shaped to approximately mirror the natural curve of the patient's soft palate 22 and uvula 24. In an example embodiment, the needle 30 is a straight needle with an 18 mm straight portion and a curved portion with a 20 mm radius. In another example embodiment, the needle 30 is a semi-curved needle with a 9 mm straight portion and a curved portion with a 27 mm radius. In another example embodiment, the needle is a curved needle with a curved portion with a 38 mm radius. Those of ordinary skill in the art will understand that the length of the needle 30 will vary according to the anatomic site.

The suture 36 is preferably a barbed suture that includes barbs 38 extending from the suture in a direction opposite to the direction of insertion of the suture. Such barbs 38 allow the suture 36 to lift, suspend and stiffen a patient's soft palate 22 and uvula 24 by grabbing the soft palate 22 and uvula 24 with the barbs 38 and allowing the doctor to pull the soft palate and/or uvula in a direction opposite or different from the insertion direction of the suture 36. In an example embodiment, the suture 36 can include bidirectional barbs. The barbs 38 eliminate the need to tie knots in the suture 36 because the barbs 38 can grab the tissue of the soft palate 22 and/or uvula 24 and distribute tension across the entire length of the tissue, which allows the soft palate 22 and/or uvula 24 to be lifted, suspended and stiffened by pulling the suture in an opposite or different direction from the direction of insertion once the suture has been inserted into the patient. One suitable suture is the Quill Knotless Tissue-Closure Device manufactured by Angiotech Pharmaceuticals, Inc. of Vancouver, Canada. In an example embodiment, size 0, 1 or 2 sutures can be used depending on the patient. In an example embodiment, the suture 36 can be pre-twisted and/or barbed in different directions and/or can include one or more knots and/or loops at an end. In an example embodiment, the center portion of the suture 36 is clear when the center portion is the first portion to enter the patient's soft palate 22. That is, the center portion of the suture 36 does not include barbs 38, which allows the center portion of the suture to be easily inserted into the soft palate 22 by folding the suture through the needle 30 or suture insertion device and causing the center portion of the suture to be the first portion of the suture inserted into the patient's soft palate. In another example embodiment, the suture 36 is dissolvable, preferably within three months. Preferably, the suture dissolves in a time period sufficient to allow the soft palate 22 to permanently suspend and stiffen the patient's soft palate 22 and/or uvula 24. Non-dissolvable sutures and sutures that dissolve in more or less than three months can also be used. An advantage of the present invention is that a doctor using the disclosed methods and apparatuses can easily alter the treatment type and suture type for patients with a wide variety of conditions.

Figure 5:
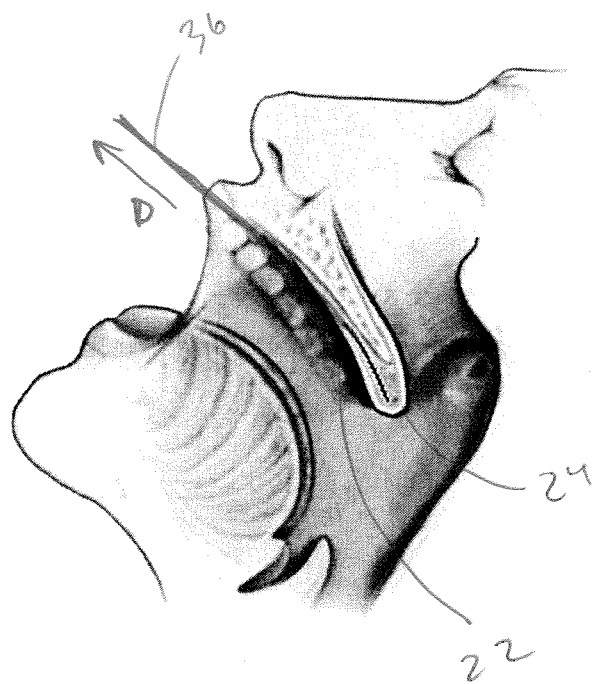
FIG. 5 is a side view illustrating an example method according to the present disclosure.

Once the suture 36 has been inserted into the patient's soft palate 22 and preferably the patient's uvula 24, it can be pulled in a direction D that is different than the insertion direction, as shown in FIG. 5. The pulling lifts the soft palate 22 and/or uvula 24 as the barbs of the suture 36 grab the patient's soft palate and/or uvula and pull the soft palate and/or uvula in the direction D of the pulling. At the same time, the pulling also stiffens the soft palate 22 by compressing the soft palate and/or uvula into a smaller area. The barbs 38 suspend the soft palate 22 and/or uvula 24 in the lifted and stiffened position once the doctor has appropriately positioned the soft palate and/or uvula. Proper placement of the suture can be verified by tugging and wiggling the suture.

In another example embodiment, the suture 36 can be inserted into the patient's soft palate 22 and uvula 24 using a triangular approach, wherein the needle 30 is inserted into a first side of the patient's soft palate 22 at an angle so that it extends to the uvula and the needle is then pushed at an angle through a second side of the soft palate 22 so that the suture 36 forms a triangle in the patient's soft palate 22 and uvula 24 and the suture 36 extends through the outer surface of the soft palate at both the first and second sides. When the needle 30 is removed, the suture 36 can be pulled from one or both of the first and second sides of the soft palate 22. The pulling lifts the soft palate 22 and/or uvula 24 as the barbs of the suture 36 grab the patient's soft palate and/or uvula and pull the soft palate and/or uvula in the direction D of the pulling. At the same time, the pulling also stiffens the soft palate 22 and/or uvula 24 by compressing the soft palate and/or uvula into a smaller area. The barbs 38 suspend the soft palate 22 and/or uvula 24 in the lifted and stiffened position once the doctor has appropriately positioned the soft palate and/or uvula. Proper placement of the suture can be verified by tugging and wiggling the suture.

Figure 6:
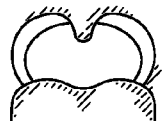
FIG. 6 shows the Ikematsu System for the Diagnosis of Snoring.
Figure 6:
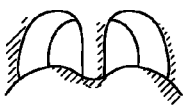
Figure 6:
Figure 6:
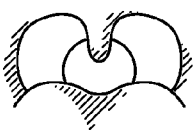
Figure 6:
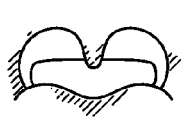
Figure 6:
Figure 6:
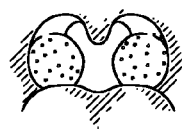
Figure 6:
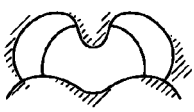
Figure 6:
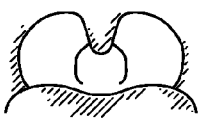
Figure 6:
Figure 6:
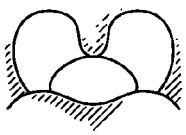
Figure 6:
Figure 6:
Figure 6:
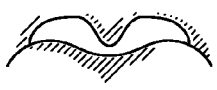
Figure 6:
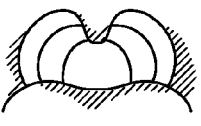

The present method of lifting, suspending and stiffening the soft palate can be titrated according to any anatomy. FIG. 6 illustrates the Ikematsu System for the Diagnosis of Snoring. One problem with current treatments for sleep apnea is that one modality of treatment does not work for all of the different uvula types shown in FIG. 6. The disclosed method can be tailored to each individual patient's specific needs. A doctor can choose one or more sutures 36 and insert the suture or sutures in one or more different locations in the patient's soft palate 22 and/or uvula 24 at one or more different angles. The disclosed method allows the doctor to adjust the patient's soft palate 22 and/or uvula 24 to an appropriate position as the treatment is being administered, giving the doctor freedom to treat each specific patient as needed.

Figure 7:
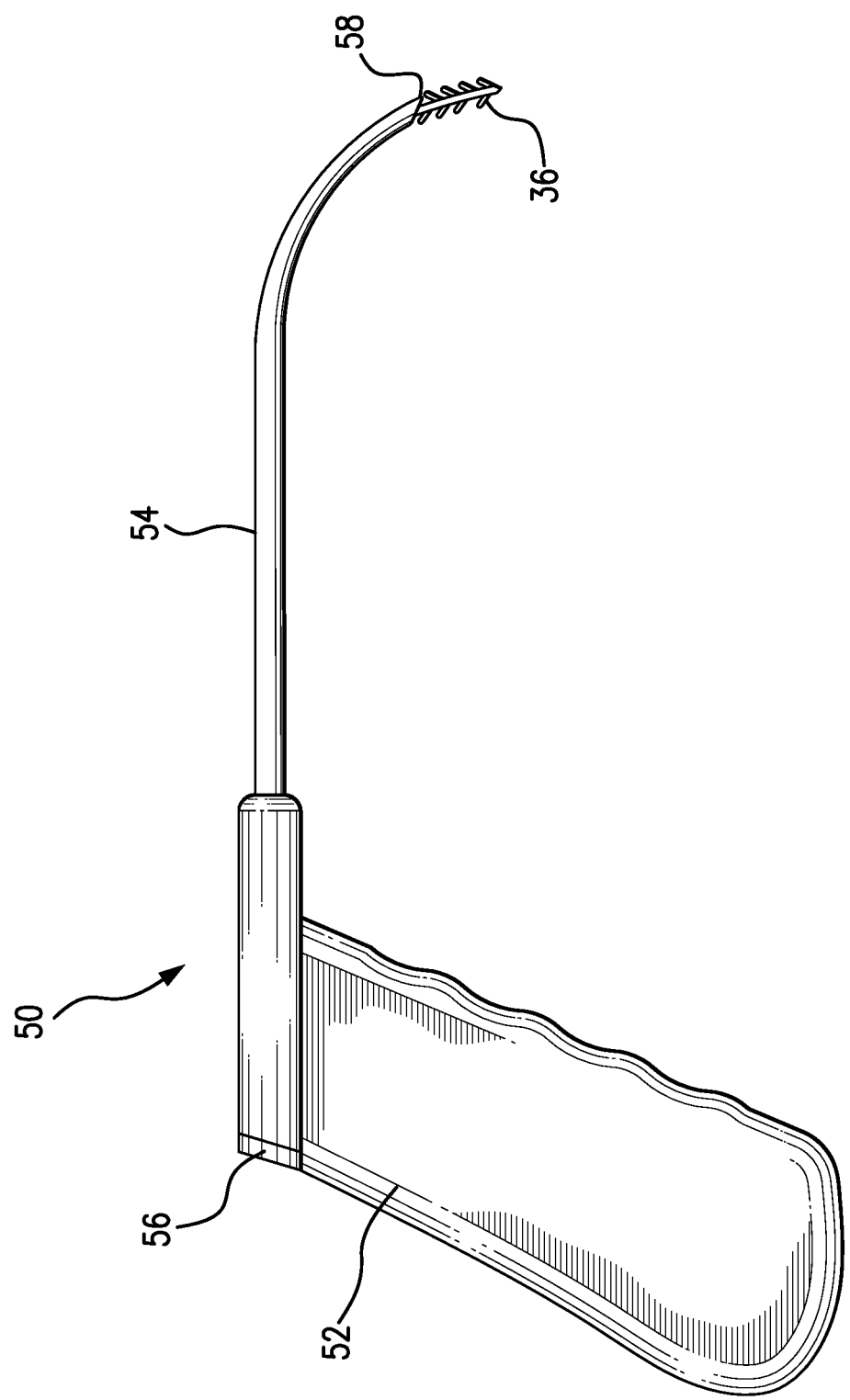
FIG. 7 is a side view of an example embodiment of a suture insertion device according to the present disclosure.

FIG. 7 illustrates an example embodiment of a suture insertion device 50 according to the present disclosure. In an example embodiment, suture insertion device 50 includes a handle 52, a piercing shaft 54 and a suture release button 56. Piercing shaft 54 includes a piercing end 58 with a sharp tip which allows piercing shaft 54 to be inserted into a patient's soft palate 22. In an example embodiment, piercing shaft 54 is a cannula. Once inserted into the soft palate, a suture 36 can be released from piercing end 58 by pressing suture release button 56. Because piercing end 56 pierces the patient's skin, suture insertion device 50 is preferably a disposable, single-use device that can be discarded after a single procedure so as not to spread infection amongst patients.

Figure 8:
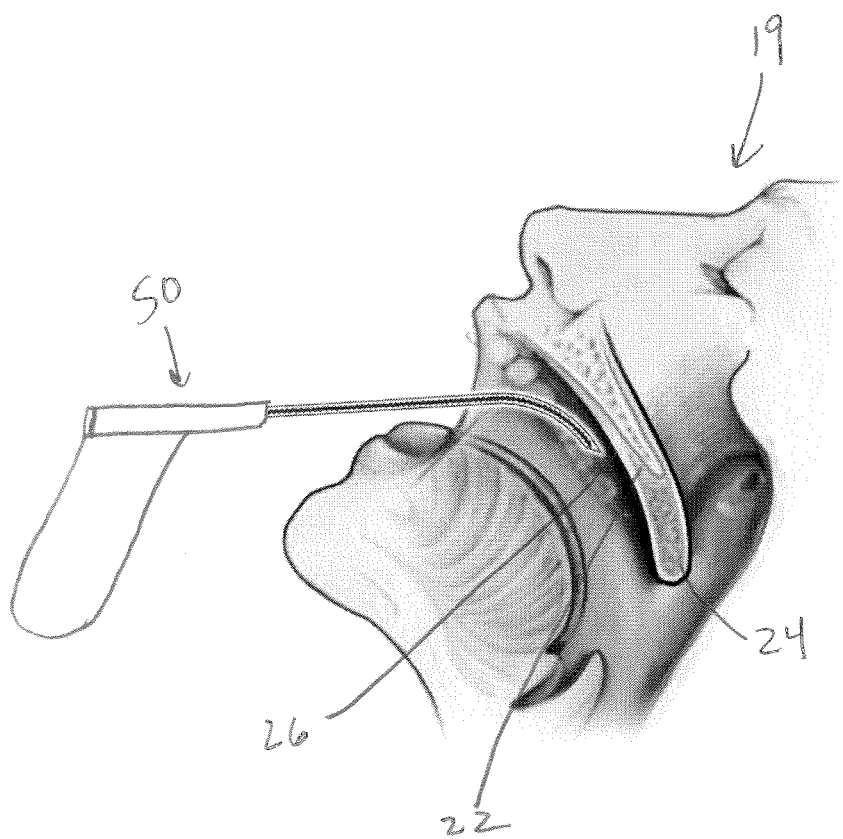
FIG. 8 is a side view of the device of FIG. 7 being inserted into a patient's soft palate.

FIGS. 8 to 14 demonstrate an example method of using suture insertion device 20 to lift and stiffen a patient's soft palate 22 and uvula 24 to open the patient's airways. FIG. 8 shows a patient 19 with an elongated uvula 24. The midline 26 of the patient's soft palate 22 is located so that piercing shaft 54 of suture insertion device 50 can be inserted into the patient's soft palate 22 at or near the midline 26 of the soft palate 22. For different types of soft palates and uvulas, the piercing shaft 54 of suture insertion device 50 can be inserted into other locations in the soft palate at other angles.

Figure 9:
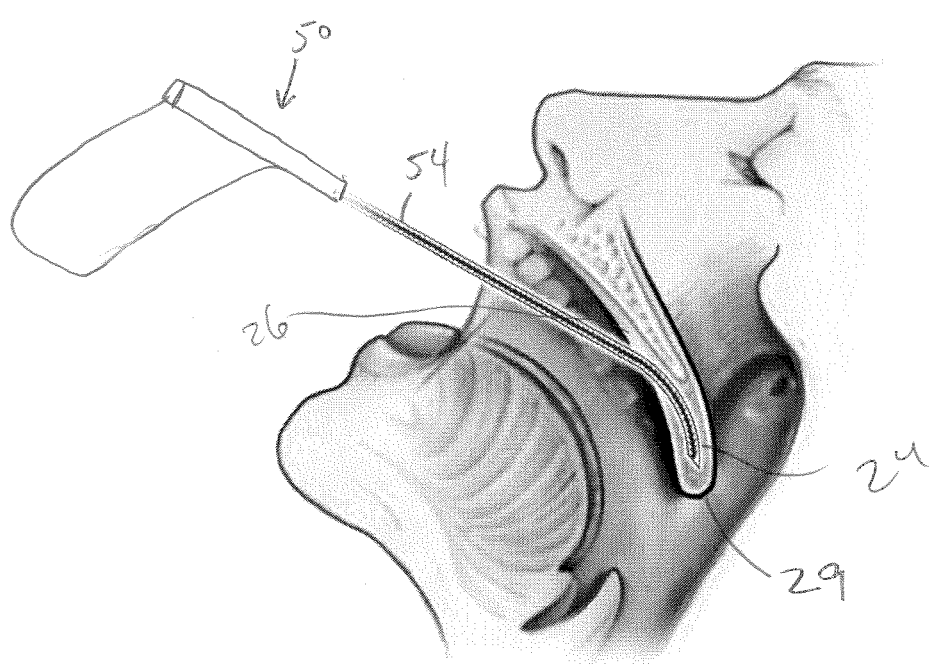
FIG. 9 is a side view of the device of FIG. 7 being inserted into a patient's soft palate.

FIG. 9 shows the piercing shaft 54 of suture insertion device 50 being inserted into the patient's soft palate 22 at a high point at the midline 26 of the soft palate 22. The placement of suture insertion device 50 should be verified.

In the illustrated embodiment, piercing shaft 54 of suture insertion device 50 is inserted into the soft palate 22 so that the piercing end 58 extends to almost the tip 29 of the uvula 24. The curve of piercing shaft 54 is designed to approximately match the curvature of the patient's soft palate 22. In other embodiments, piercing shaft 54 of suture insertion device 50 is inserted into the soft palate 22 so that the piercing end 58 extends to different locations in the soft palate. Piercing shaft 54 can optionally include depth markings so that the doctor performing the procedure can accurately determine how far the piercing shaft 54 has been inserted into the patient's soft palate 22. In an example embodiment, piercing shaft 54 includes an 18 mm straight portion and a curved portion with a 20 mm radius. In another example embodiment, piercing shaft 54 includes a 9 mm straight portion and a curved portion with a 27 mm radius. In another example embodiment, piercing shaft 54 includes a curved portion with a 38 mm radius. Those of ordinary skill in the art will understand that the length and curvature of piercing shaft 54 will vary according to the anatomic site.

Figure 10:
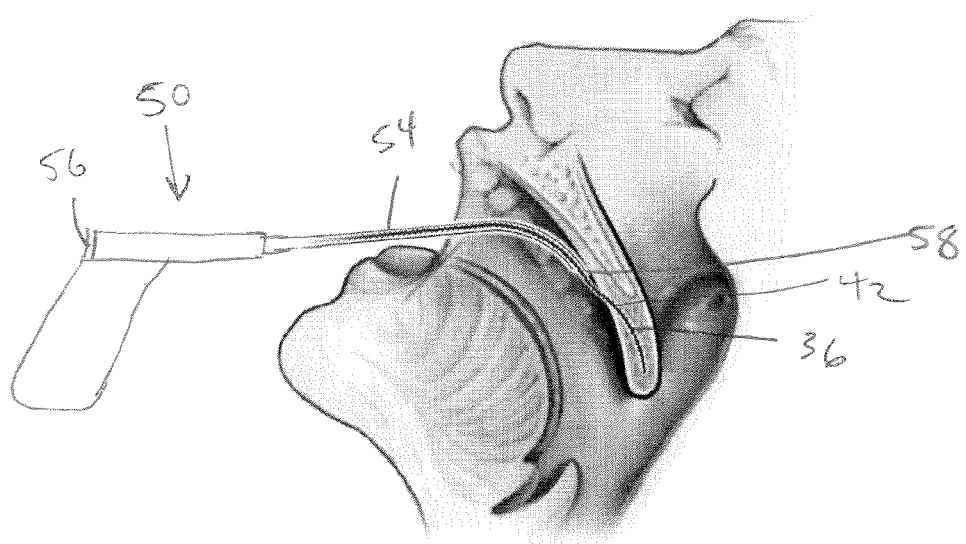
FIG. 10 is a side view of the device of FIG. 7 being removed from a patient's soft palate.
Figure 11:
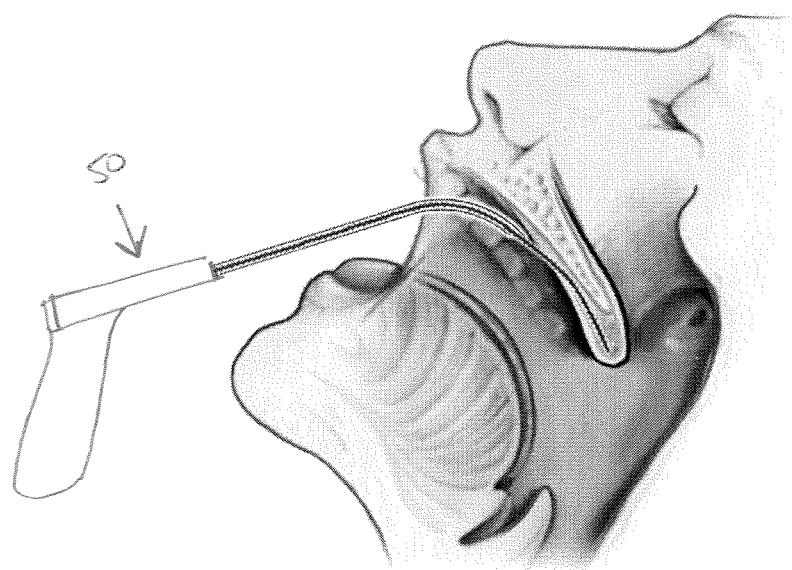
FIG. 11 is a side view of the device of FIG. 7 being removed from a patient's soft palate.

FIG. 10 shows the release of suture 36 from piercing shaft 54 of suture insertion device 50. Once piercing shaft 54 of suture insertion device 50 has been appropriately positioned and the position has been verified, suture 36 can be released from piercing end 58 by pressing suture release button 56. As the suture 36 is released from piercing shaft 54, piercing shaft 54 is withdrawn from the patient's soft palate 22. The barbs 38 on suture 36 grab the patient's uvula 24 and/or soft palate 22 and hold suture 36 in place as piercing shaft 54 is withdrawn. FIG. 11 shows the release of a length 42 of suture 36 as the piercing shaft 54 of suture insertion device 50 is completely withdrawn from the patient's soft palate 22. In one example embodiment, suture release button 56 can release suture 36 continuously. In another example embodiment, suture release button 56 can release suture 36 in discrete increments.

Figure 12:
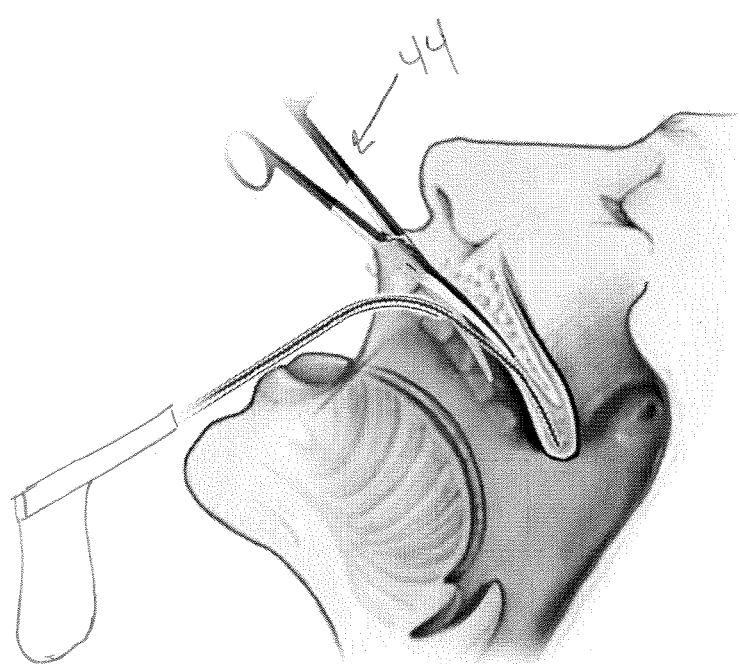
FIG. 12 is a side view of the device of FIG. 7 being removed from a patient's soft palate.

FIG. 11 shows the patient's soft palate 22 and uvula 24 being elevated. Once the piercing shaft 54 has been withdrawn from the patient's soft palate 22, suture release button 56 is released so that suture 36 ceases to be released from piercing shaft 54. Once the suture 36 ceases to be released, suture insertion device 50 can be pulled in a direction different than the insertion direction to elevate the patient's palate 22 and raise the patient's uvula 24. The pulling lifts the soft palate 22 and uvula 24 as the barbs 38 of the suture 36 grab the patient's soft palate and uvula and pull the soft palate and uvula in the direction of the pulling. The pulling also stiffens the soft palate 22 and uvula 24 by compressing the soft palate and uvula into a smaller area. The barbs 38 suspend the soft palate 22 and/or uvula 24 in the lifted and stiffened position once the doctor has appropriately positioned the soft palate and/or uvula. Proper placement of the suture can be verified by tugging and wiggling the suture. Once the patient's palate is accurately positioned, the suture 36 can be cut from piercing shaft 54 using a cutting device 44. Cutting device 44 can be a scissors as shown in FIG. 12, or it can be any other device separate from suture insertion device 50 and capable of cutting suture 36. In an alternative embodiment, cutting device 44 can be part of suture insertion device 50 and can cut suture 36 with, for example, the press of a button. Such an alternative embodiment is advantageous in that it simplifies the process and reduces the tooling. Using a separate cutting device is alternatively advantageous in that the suture insertion device 50 can be more cheaply manufactured as a disposable single-use device which can be discarded after a single procedure. Further alternatively, suture 36 can be cut from suture insertion device 50 before the patient's soft palate 22 has been elevated and the patient's uvula 24 has been raised. A doctor can then grab the suture with his or her hands to perform the lifting and stiffening described above.

Figure 13:
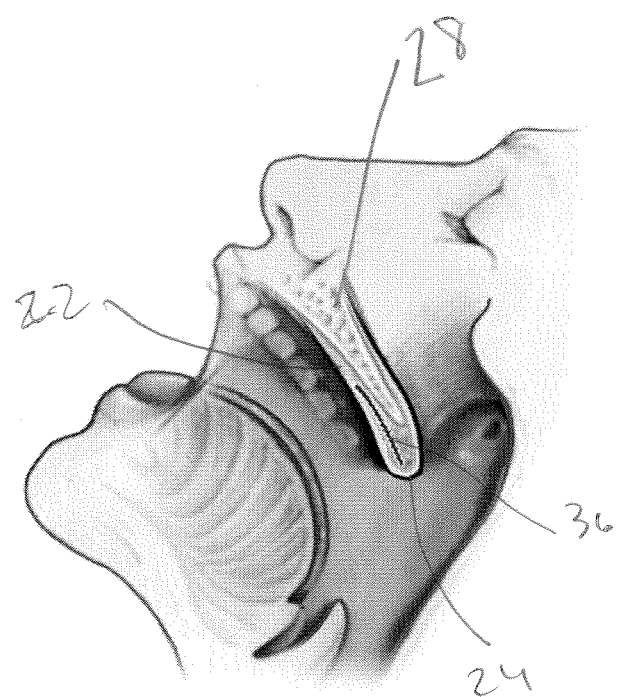
FIG. 13 is a side view of an example patient that has been treated with the device of FIG. 7.
Figure 14:
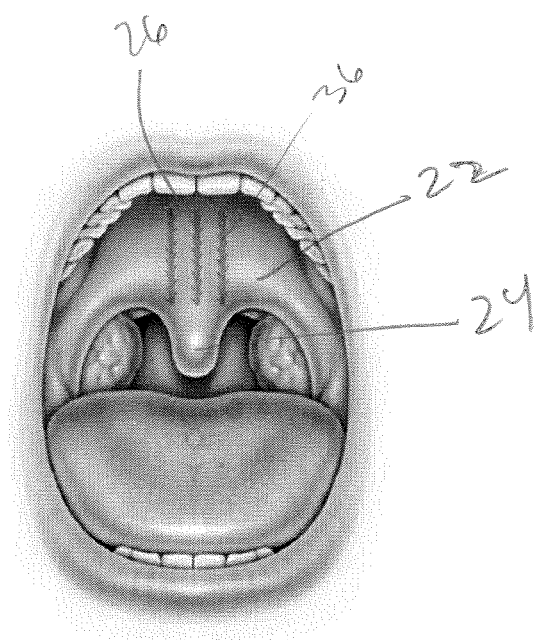
FIG. 14 is a front view of an example patient that has been treated with the device of FIG. 7.

The process can then be repeated with as many sutures 36 as necessary to lift, suspend and stiffen the patient's soft palate 22 and/or uvula 24. The sutures 36 can be inserted in different parts of the patient's soft palate 22 and/or uvula 24 and can be inserted at different angles. FIGS. 13 and 14 show a side view and a front view, respectively, of an example embodiment of a patient's mouth once three sutures 36 have been placed in the patient's soft palate. In the example embodiment shown, the three sutures 36 have been inserted into the patient's soft palate 22 side by side at the midline 26 between the patient's hard palate 28 and soft palate 22. In another example embodiment, the suture 36 can be inserted into the patient's soft palate 22 and uvula 24 using the triangular approach described above, wherein the piercing shaft 54 is inserted into a first side of the patient's soft palate 22 at an angle so that the piercing shaft extends to the uvula and the piercing shaft 54 is then pushed at an angle through a second side of the soft palate 22 so that the suture 36 forms a triangle in the patient's soft palate 22 and uvula 24 and the suture 36 extends through the outer surface of the soft palate at both the first and second sides.

Figure 15:
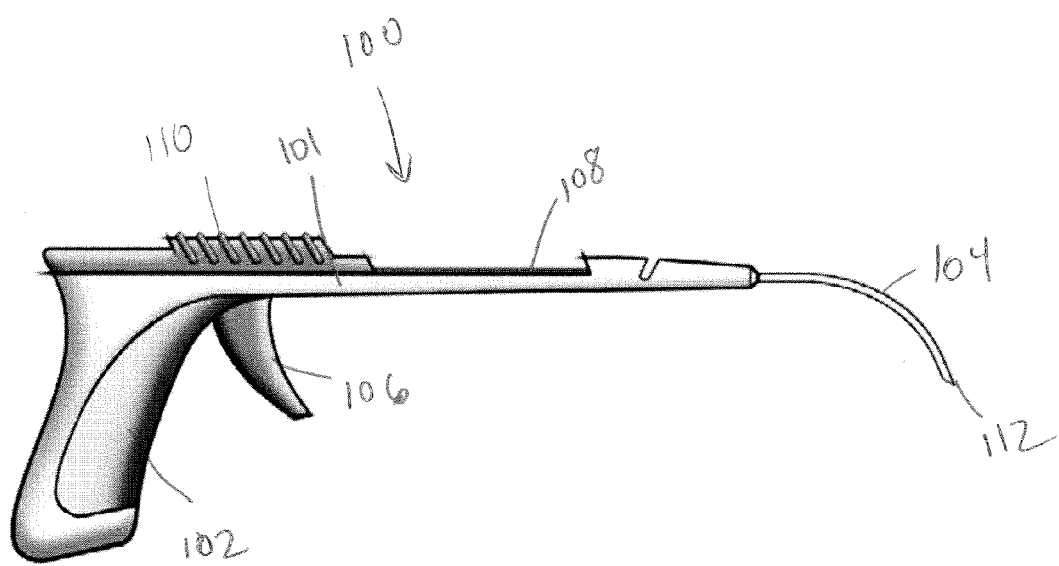
FIG. 15 is a side view of an example embodiment of a suture insertion device according to the present disclosure.

FIG. 15 illustrates another example embodiment of a suture insertion device 100 according to the present disclosure. In an example embodiment, suture insertion device 100 includes a main body 101, a handle 102, a piercing shaft 104, a suture release button 106, an insertion shaft 108 and an insertion shaft adjustment 110. Piercing shaft 104 includes a piercing end 112 with a sharp tip that allows piercing shaft 104 to be inserted into a patient's soft palate 22. In an example embodiment, piercing shaft 104 is a cannula and insertion shaft 108 is moveable within the cannula. Once inserted into the soft palate 22, insertion shaft 108 can be deployed from inside piercing shaft 104 so as to deploy a length of a suture 36. Because piecing end 112 pierces a patient's skin, suture insertion device 100 is preferably a disposable, single-use device that can be discarded after a single procedure so as not to spread infection amongst patients.

FIGS. 16 to 22 demonstrate an example method of using suture insertion device 100 to lift and stiffen a patient's soft palate 22 and/or uvula 24 to open the patient's airways. Preferably, suture insertion device 100 is not preloaded with a suture. Instead, suture insertion device can be loaded with any type of suture that a doctor chooses to best treat a specific patient.

Figure 16:
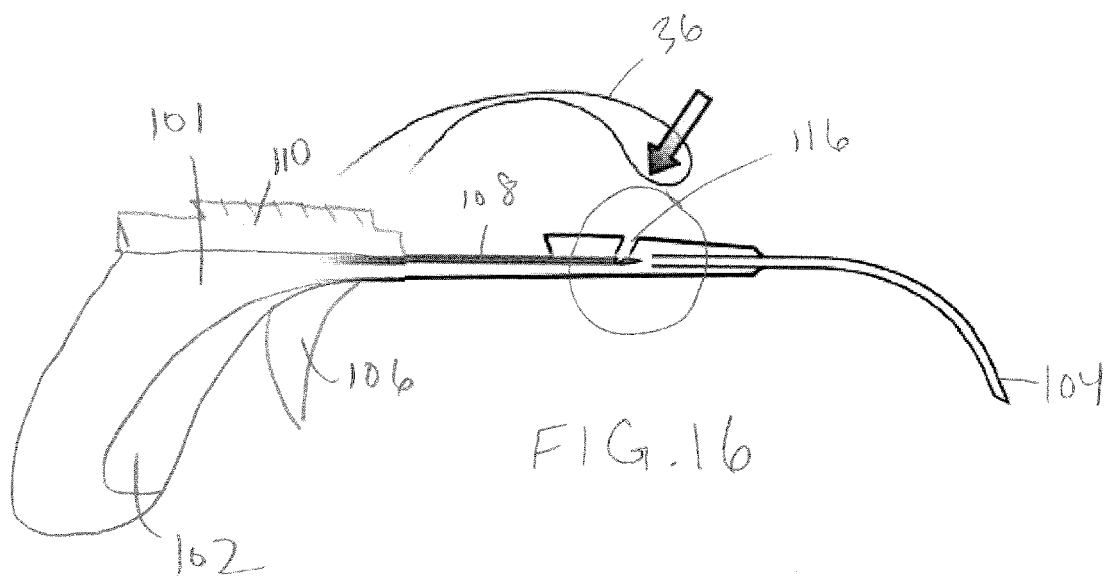
FIG. 16 is a side view of the device of FIG. 14.
Figure 17:
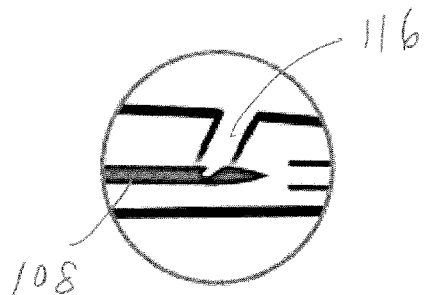
FIG. 17 is a detailed view from FIG. 16.
Figure 18:
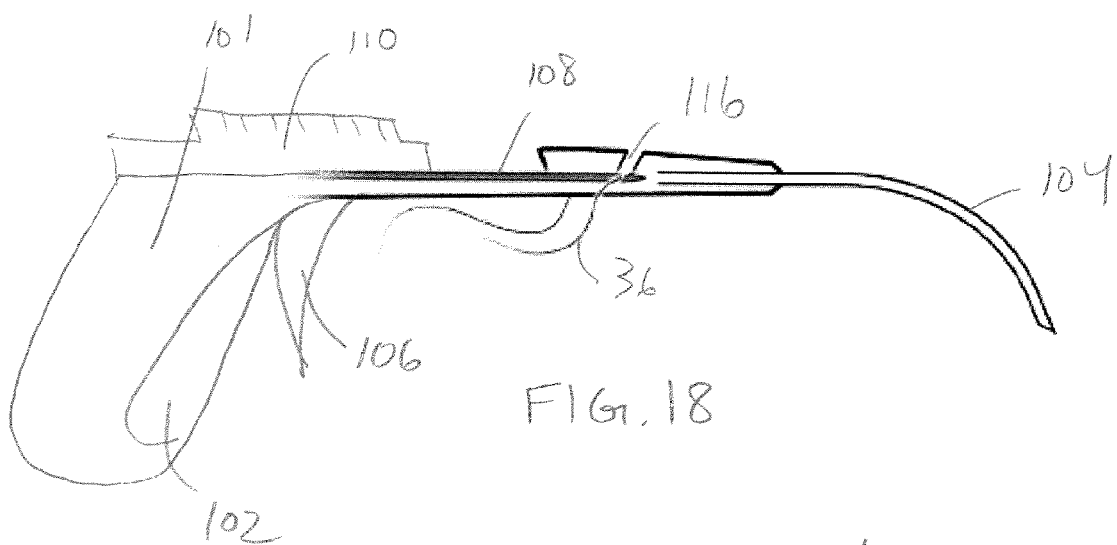
FIG. 18 is a side view of the device of FIG. 14.
Figure 19:
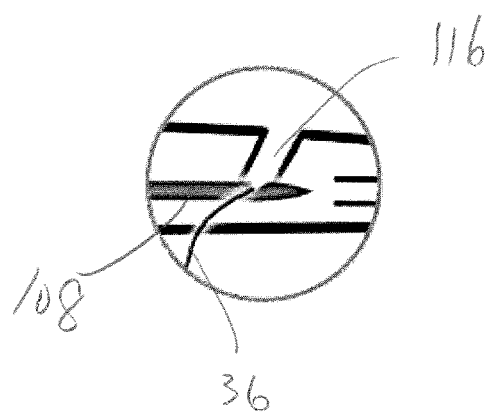
FIG. 19 is a detailed view from FIG. 18.

FIGS. 16 and 18 show cross-sectional views of suture insertion device 100 in a first, loading configuration. In the first, loading configuration, insertion shaft adjustment 110 is in a loading position such that the end of insertion shaft 108 is located at a threading notch 116 of suture insertion device 100. FIGS. 17 and 19 show a blown-up view of suture insertion device 100 at threading notch 116. A center portion of a suture 36 can be looped into the threading notch 116 and attached to or hooked onto the end of insertion shaft 108. Insertion shaft 108 can then pull suture 36 through piercing shaft 104 for insertion into a patient's soft palate 22 and/or uvula 24. Since the center portion of the suture 36 will be the first portion of the suture to contact and enter the patient's soft palate 22 and/or uvula 24 upon deployment of the insertion shaft 108 out of the piercing shaft 104, the center portion of the suture 36 is preferably clear (no barbs), which allows the center portion of the suture 36 to be more easily inserted into the soft palate 22.

Figure 20:
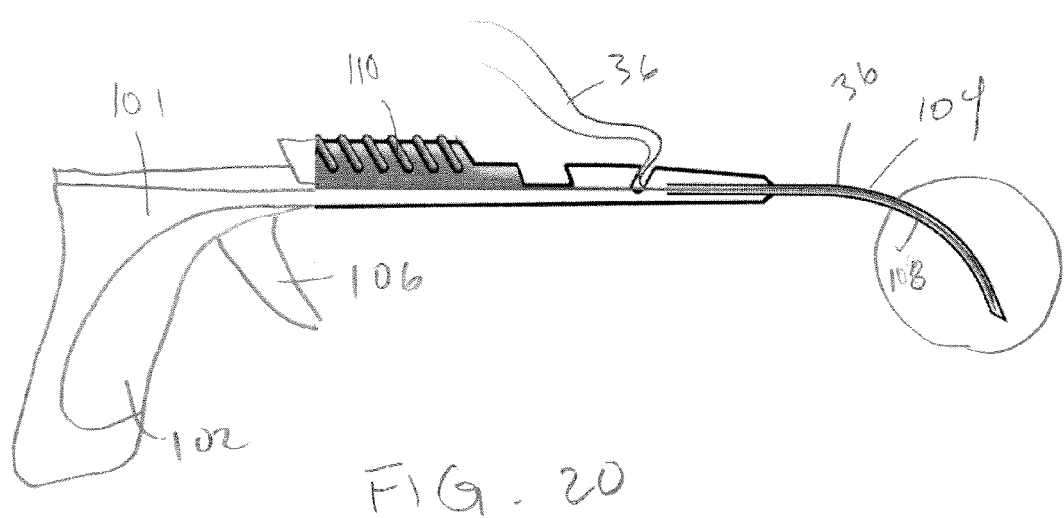
FIG. 20 is a side view of the device of FIG. 14.
Figure 21:
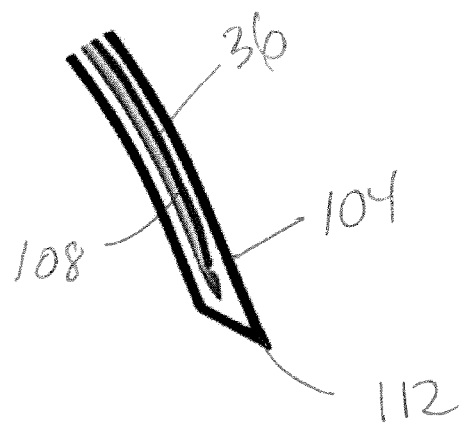
FIG. 21 is a detailed view from FIG. 20.

Once the suture 36 is attached to the end of insertion shaft 108, insertion shaft 108 can be moved to a second, intermediate configuration wherein insertion shaft 108 is pushed towards the front of piercing shaft 104 but does not extend past the piercing end 112 of piercing shaft 104. In the illustrated embodiment, suture release button 106 can be used to move insertion shaft from the first position to the second position. Alternatively, insertion shaft adjustment 110 can be used to move insertion shaft 108 from the first position to the second position. FIG. 20 shows a cross-sectional view with insertion shaft 108 in the second, intermediate position, and FIG. 21 shows a blown up view of insertion shaft 108 at the piercing end 112 of piercing shaft 104. As the insertion shaft 108 is pushed forward through piercing shaft 104, the attached suture 36 is also drawn through the piercing shaft 104.

Figure 22:
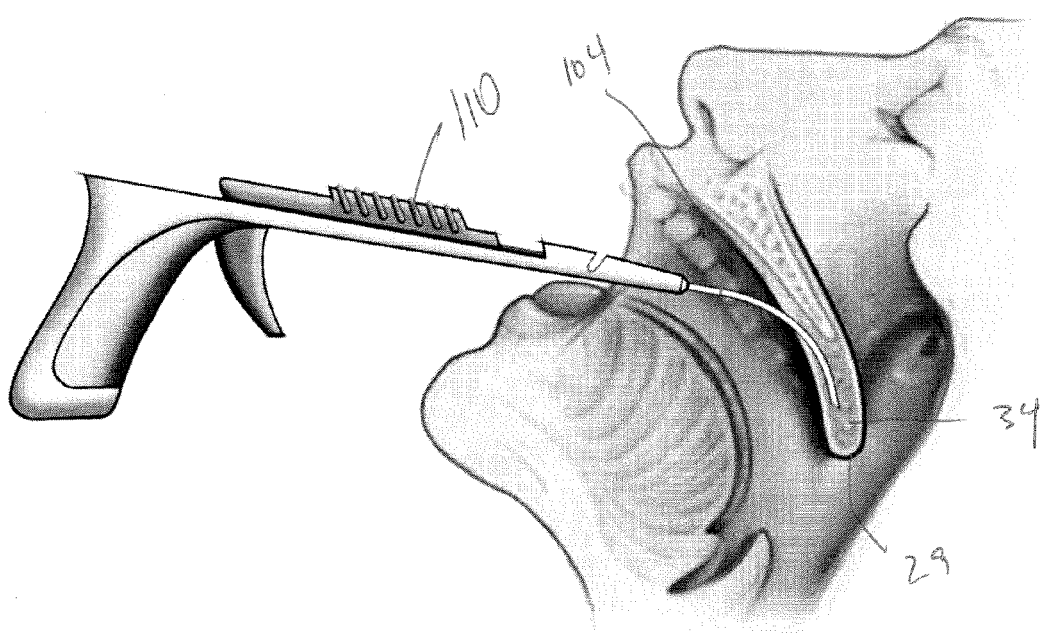
FIG. 22 is a side view of the device of FIG. 14 being inserted into a patient's soft palate.

FIG. 22 shows suture insertion device 100 being inserted into a patient's soft palate 22 at a high point at the midline of the soft palate 22. The placement of suture insertion device 100 should be verified. In the illustrated embodiment, piercing shaft 104 of suture insertion device 100 is inserted into the soft palate so that the piercing end 112 extends to almost the tip 29 of the patient's uvula 24. In other embodiments, piercing shaft 104 of suture insertion device 100 is inserted into the soft palate so that the piercing end 112 extends to different locations in the soft palate. The curve of piercing shaft 104 is designed to approximately match the curvature of the patient's soft palate 22. Piercing shaft 104 can optionally include depth markings so that the doctor performing the procedure can accurately determine how far the piercing shaft 104 has been inserted into the patient's soft palate 22. In an example embodiment, piercing shaft 104 includes an 18 mm straight portion and a curved portion with a 20 mm radius. In another example embodiment, piercing shaft 104 includes a 9 mm straight portion and a curved portion with a 27 mm radius. In another example embodiment, piercing shaft 104 includes a curved portion with a 38 mm radius. Those of ordinary skill in the art will understand that the length and curvature of piercing shaft 54 will vary according to the anatomic site.

Figure 23:
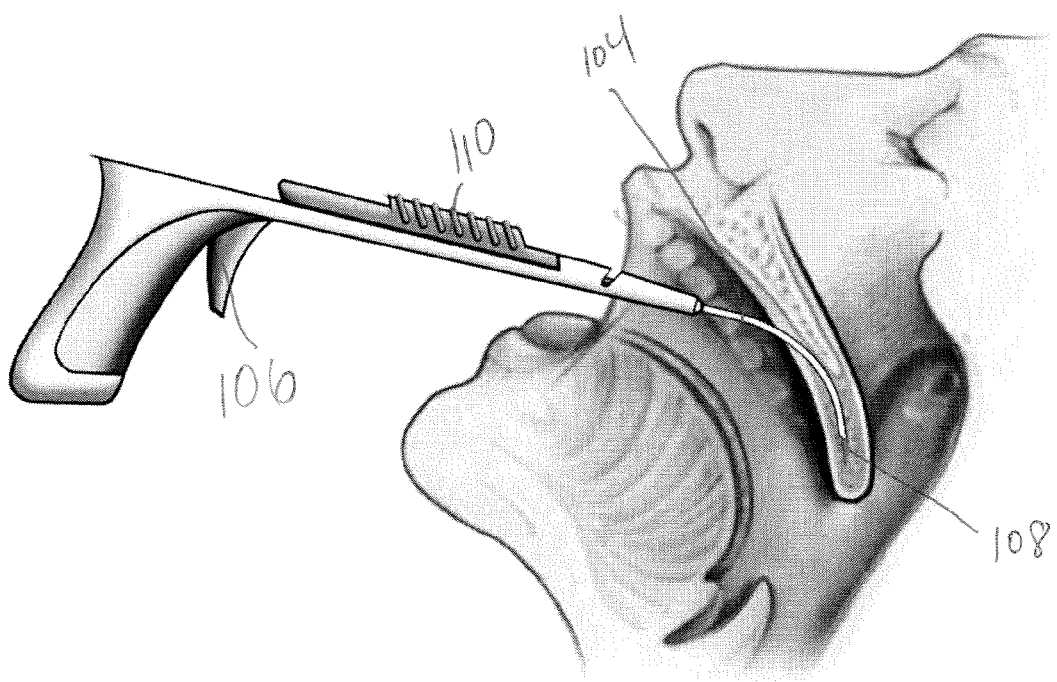
FIG. 23 is a side view of the device of FIG. 14 being inserted into a patient's soft palate.
Figure 24:
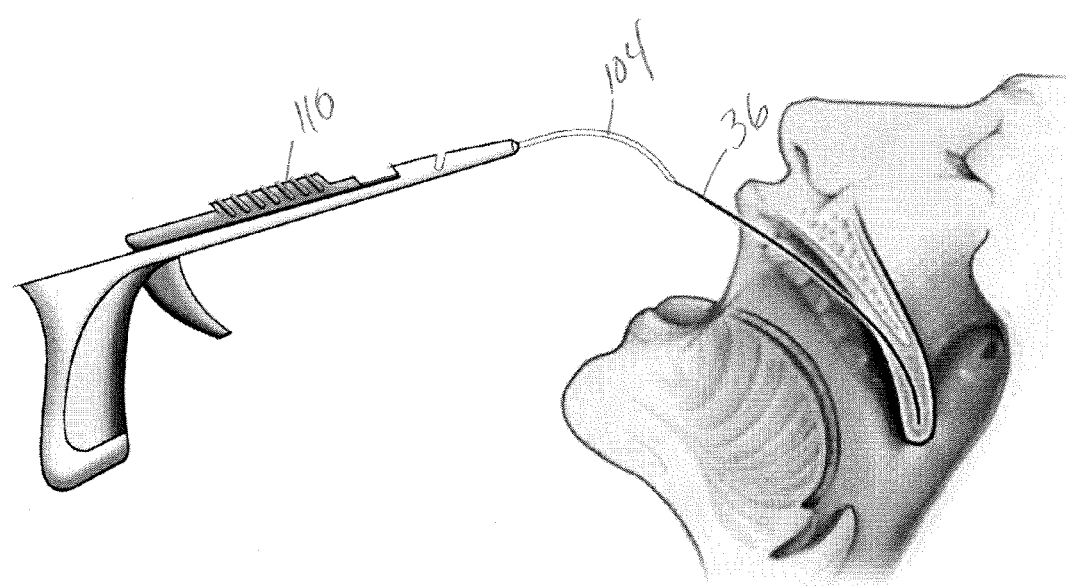
FIG. 24 is a side view of the device of FIG. 14 being removed from a patient's soft palate.

Once the piercing shaft 104 has been inserted into the patient's soft palate 22, insertion shaft adjustment 110 can be moved to a third, deployed configuration wherein the insertion shaft 108 is pushed out of piercing shaft 104 and past the piercing end 112 of piercing shaft 104. FIG. 23 shows the third, deployed position. In an example embodiment, insertion shaft 108 is pushed out of the piercing shaft 104 and past the piercing end 112 of piercing shaft 104 by pulling suture release button 106. Alternatively, insertion shaft 108 can be pushed out of the piercing shaft 104 and past the piercing end 112 of piercing shaft 104 using insertion shaft adjustment 110. The release of insertion shaft 108 from piercing shaft 104 also releases the attached suture 36 from piercing shaft 104. The barbs 38 on suture 36 grab the patient's uvula 24 and/or soft palate 22 and hold suture 36 in place as piercing shaft 104 and insertion shaft 108 are withdrawn from the patient's soft palate 22. FIG. 24 shows the release of a length of suture 36 as piercing shaft 104 and insertion shaft 108 are withdrawn from the patient's soft palate 22. Once the suture has been released into the patient's soft palate 22 and/or uvula 24, insertion shaft 108 can be drawn back inside piercing shaft 108 in the intermediate position, or insertion shaft can remain in the deployed position. The barbs 38 of suture 36 will hold suture 36 within the patient's soft palate 22 and/or uvula 24. FIG. 24 shows the insertion shaft 108 drawn back into the intermediate position as piercing shaft 104 is withdrawn from the patient's soft palate 22.

Figure 25:
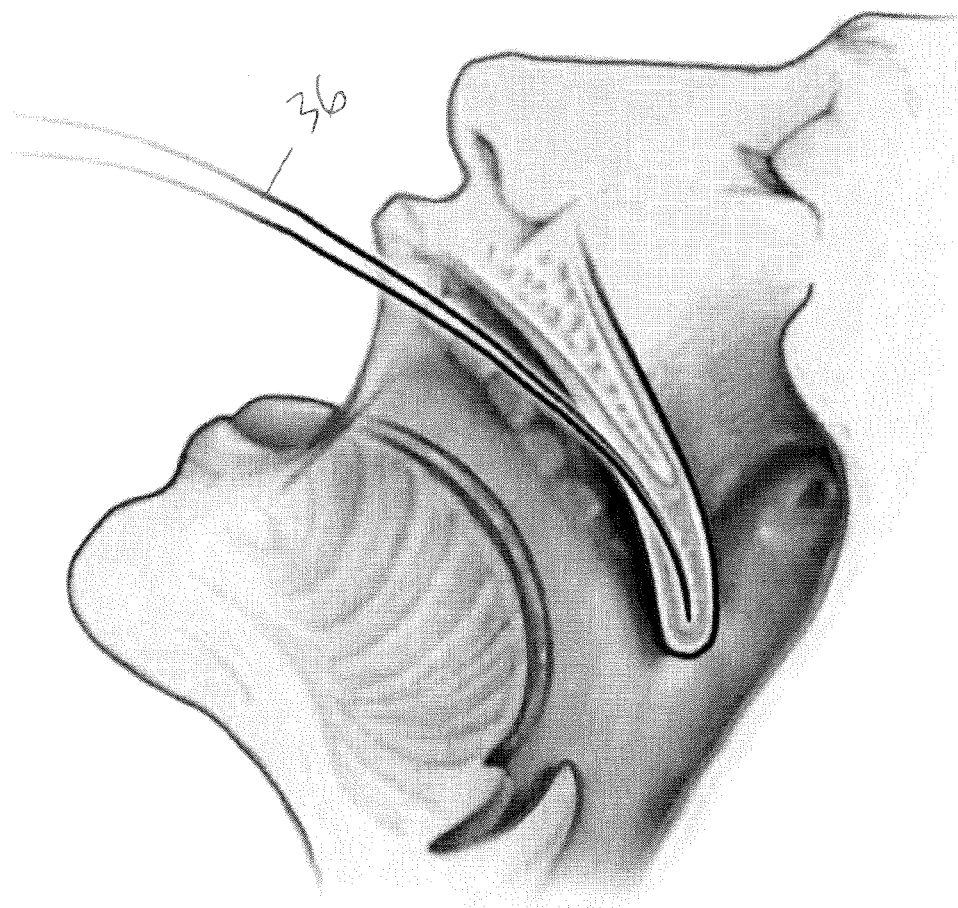
FIG. 25 is a side view of the device of FIG. 14 being removed from a patient's soft palate.

FIG. 25 shows the patient's palate being elevated. Once piercing shaft 104 has been withdrawn from the patient's soft palate 22, the patient's soft palate 22 and/or uvula 24 can be lifted, suspended and stiffened by pulling the suture 36 in a direction different from the insertion direction of the piercing shaft 104. The pulling lifts the soft palate 22 and/or uvula 24 as the barbs 38 of the suture 36 grab the patient's soft palate and/or uvula and pull the soft palate and/or uvula in the direction of the pulling. The pulling also stiffens the soft palate 22 and/or uvula 24 by compressing the soft palate and/or uvula into a smaller area. The barbs 38 suspend the soft palate 22 and/or uvula 24 in the lifted and stiffened position once the doctor has appropriately positioned the soft palate and/or uvula. Proper placement of the suture 36 can be verified by tugging and wiggling the suture. In an example embodiment, the center portion and/or another portion of suture 36 can include a sealing element so that the patient's soft palate 22 and/or uvula 24 will not be released from suture 36 over time. In one embodiment, the sealing element can be a tissue sealant to secure or fix the cut end of the suture and achieve long term lifting of the palate. In another embodiment, the sealing element can be a knot or clip to secure or fix the cut end of the suture and achieve long term lifting of the palate. In yet another example embodiment, the suture 36 can be inserted into the patient's soft palate 22 and uvula 24 using the triangular approach described above.

Figure 26:
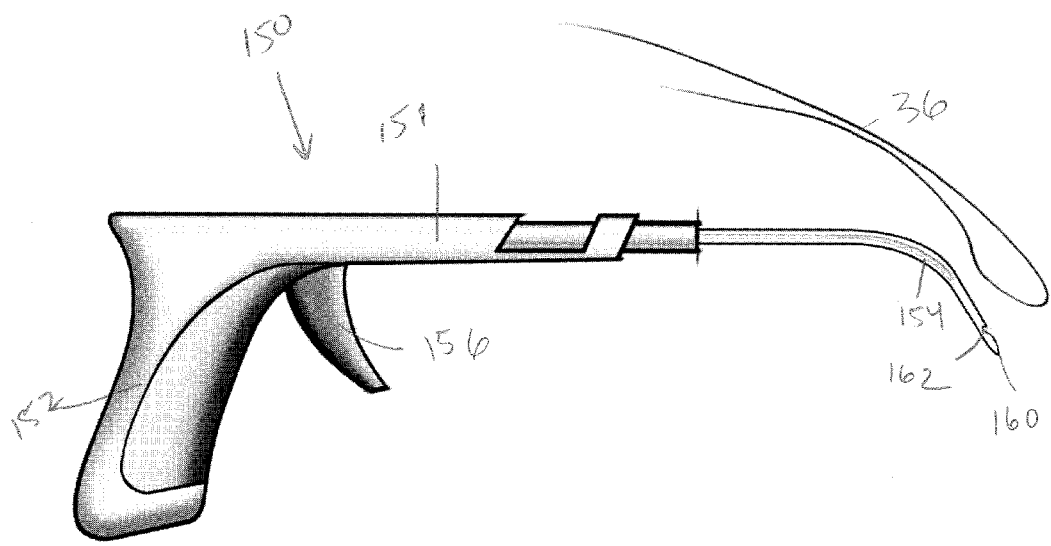
FIG. 26 is a side view of an example embodiment of a suture insertion device according to the present disclosure.

FIG. 26 illustrates yet another example embodiment of a suture insertion device 150 according to the present disclosure. In an example embodiment, suture insertion device 150 includes a main body 151, a handle 152, a piercing shaft 154, a suture release button 156, and an insertion shaft 158. Piercing shaft 154 includes a piercing end 160 with a sharp tip that allows piercing shaft 154 to be inserted into a patient's soft palate 22. In an example embodiment, piercing shaft 154 is a cannula and tapers toward the piercing end 160, and insertion shaft 158 is moveable within the cannula. In another example embodiment, piercing shaft 154 is about 36 mm in length, with the percutaneous end being 18 mm in length. Once inserted into the soft palate 22, insertion shaft 158 can be deployed from piercing shaft 154 so as to deploy a length of a suture 36. Because piecing end 150 pierces a patient's skin, suture insertion device 150 is preferably a disposable, single-use device that can be discarded after a single procedure so as not to spread infection amongst patients.

FIGS. 26 to 30 demonstrate an example method of using suture insertion device 150 to lift, suspend and stiffen a patient's soft palate 22 to open the patient's airways. Preferably, suture insertion device 150 is not preloaded with a suture 36. Instead, suture insertion device 150 can be loaded with any type of suture 36 that a doctor chooses to best treat a specific patient.

FIG. 26 shows suture insertion device 150 in a first, loading configuration. In the loading configuration, insertion shaft 158 is in a loading position such that insertion shaft 158 is located within piercing shaft 154 but does not extend past threading notch 162 of piercing shaft 154. A center portion of a suture 36 can be looped into threading notch 162. Since the center portion of the suture 36 will be the first portion of the suture to contact and enter the patient's soft palate 22 and/or uvula 24 upon deployment of the insertion shaft 158 out of the piercing shaft 154, the center portion of the suture 36 is preferably clear (no barbs), which allows the center portion of the suture to be more easily inserted into the soft palate.

Figure 27:
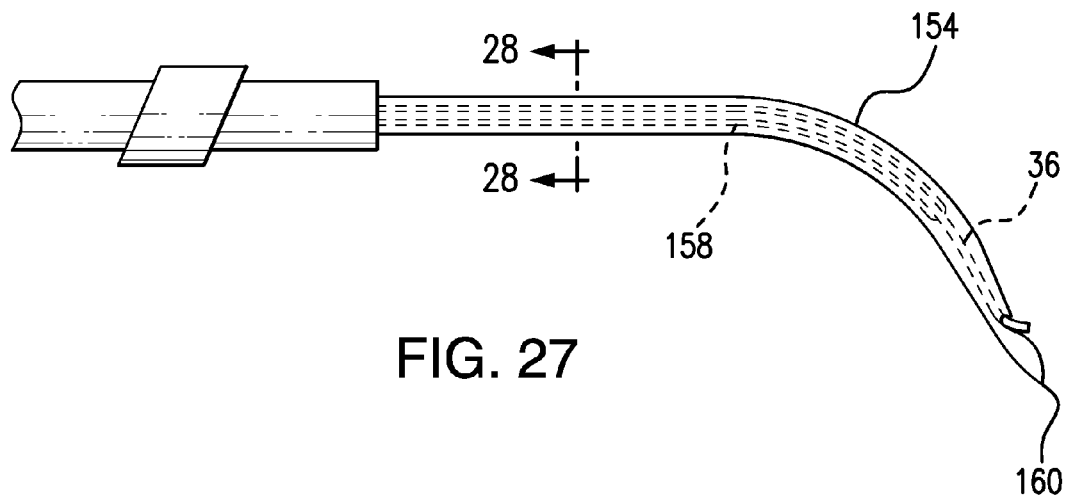
FIG. 27 is a detailed view from FIG. 26.
Figure 28:
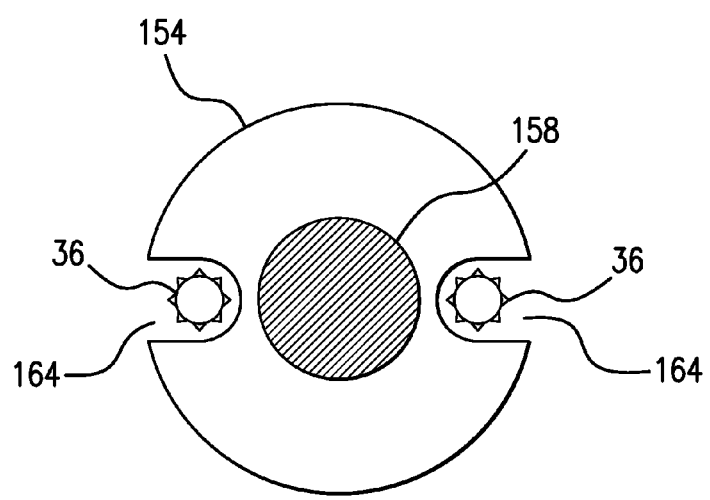
FIG. 28 is a cross-sectional view taken across lines 28-28 in FIG. 27.

FIGS. 27 and 28 illustrate a blown-up view and a cross sectional view, respectively, of piercing shaft 154 after a suture 36 has been looped into threading notch 162. At this stage, insertion shaft 158 remains in the loading position and does not contact suture 36. As illustrated in FIG. 28, the outer portion of piercing shaft 154 includes two suture-retaining grooves 164. While suture insertion device 150 is in the loading configuration, suture 36 can be looped over threading notch 162 and threaded through the two suture-retaining grooves 164. The suture-retaining grooves 164 allow the suture 36 to remain outside piercing shaft 154 so that piercing shaft 154 can be inserted into a patient's soft palate 22 without the barbs 38 of the suture 36 grabbing the patient's soft palate 22 until the doctor performing the procedure releases the suture 36 from piercing shaft 154. FIGS. 27 and 28 show the suture 36 after the suture has been looped over threading notch 162 and threaded through the two suture-retaining grooves 164.

Figure 29:
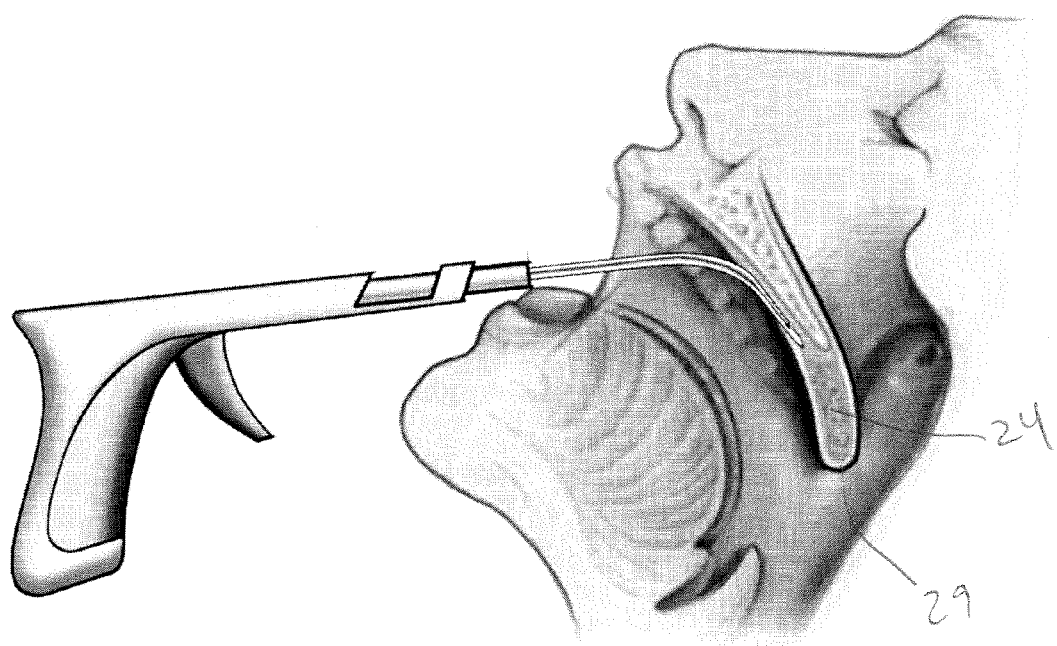
FIG. 29 is a side view of the device of FIG. 26 being inserted into a patient's soft palate.

FIG. 29 shows suture insertion device 150 being inserted into the patient's soft palate 22 at a high point at the midline of the soft palate 22. The placement of suture insertion device 150 should be verified. In the illustrated embodiment, piercing shaft 154 of suture insertion device 150 is inserted into the soft palate 22 so that the piercing end 160 extends to almost the tip 29 of the patient's uvula 24. In other embodiments, piercing shaft 154 of suture insertion device 150 can be inserted into the soft palate 22 so that the piercing end 160 extends to different locations in the soft palate. The curve of piercing shaft 154 is designed to approximately match the curvature of the patient's soft palate 22. The piercing shaft 154 can optionally include depth markings so that the doctor performing the procedure can accurately determine how far the piercing shaft 154 has been inserted into the patient's soft palate. In an example embodiment, piercing shaft 154 includes an 18 mm straight portion and a curved portion with a 20 mm radius. In another example embodiment, piercing shaft 154 includes a 9 mm straight portion and a curved portion with a 27 mm radius. In another example embodiment, piercing shaft 154 includes a curved portion with a 38 mm radius. Those of ordinary skill in the art will understand that the length and curvature of piercing shaft 54 will vary according to the anatomic site.

Figure 30:
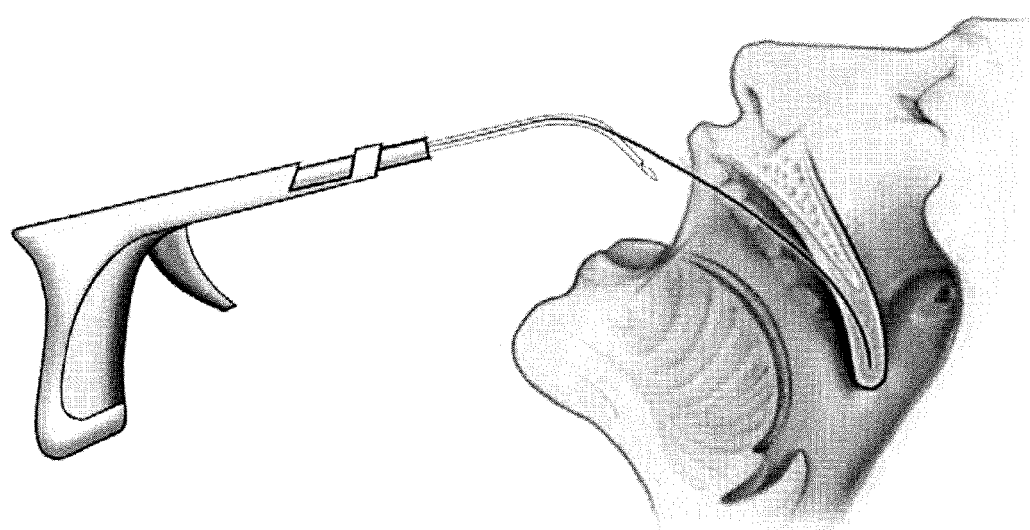
FIG. 30 is a side view of the device of FIG. 26 being removed from a patient's soft palate.

Once the piercing shaft 154 has been inserted into the patient's soft palate 22 and/or uvula 24, suture release button 156 can be pressed so that insertion shaft 158 moves through threading notch 162 and out of piercing shaft 154. As insertion shaft 158 moves through threading notch 162, insertion shaft 158 forces suture 36 out of threading notch 162 so that the barbs 38 of suture 36 move out of suture-retaining grooves 164 and grab the patient's soft palate 22 and/or uvula 24. The barbs 38 on suture 36 grab the patient's soft palate 22 and/or uvula 24 and hold suture 36 in place as piercing shaft 154 and insertion shaft 158 are withdrawn from the patient's soft palate 22. FIG. 30 shows the release of a length of suture 36 as piercing shaft 154 is withdrawn from the patient's soft palate 22. Once piercing shaft 154 has been withdrawn from the patient's soft palate, the patient's soft palate 22 and/or uvula 24 can be lifted, suspended and stiffened by pulling the suture 36 in a direction different from the insertion direction of the piercing shaft 154. The pulling lifts the soft palate 22 and/or uvula 24 as the barbs of the suture 36 grab the patient's soft palate and/or uvula and pull the soft palate and/or uvula in the direction of the pulling. The pulling also stiffens the soft palate 22 and/or uvula 24 by compressing the soft palate and/or uvula into a smaller area. The barbs 38 suspend the soft palate 22 and/or uvula 24 in the lifted and stiffened position once the doctor has appropriately positioned the soft palate and/or uvula. Proper placement of the suture 36 can be verified by tugging and wiggling the suture. In an example embodiment, the center portion and/or another portion of suture 36 can include a sealing element so that the patient's soft palate 22 and/or uvula 24 will not be released over time. In one embodiment, the sealing element can be a tissue sealant to secure or fix the cut end of the suture and achieve long term lifting of the palate. In another embodiment, the sealing element can be a knot or clip to secure or fix the cut end of the suture and achieve long term lifting of the palate. In yet another example embodiment, the suture 36 can be inserted into the patient's soft palate 22 and uvula 24 using the triangular approach described above.

Figure 31:
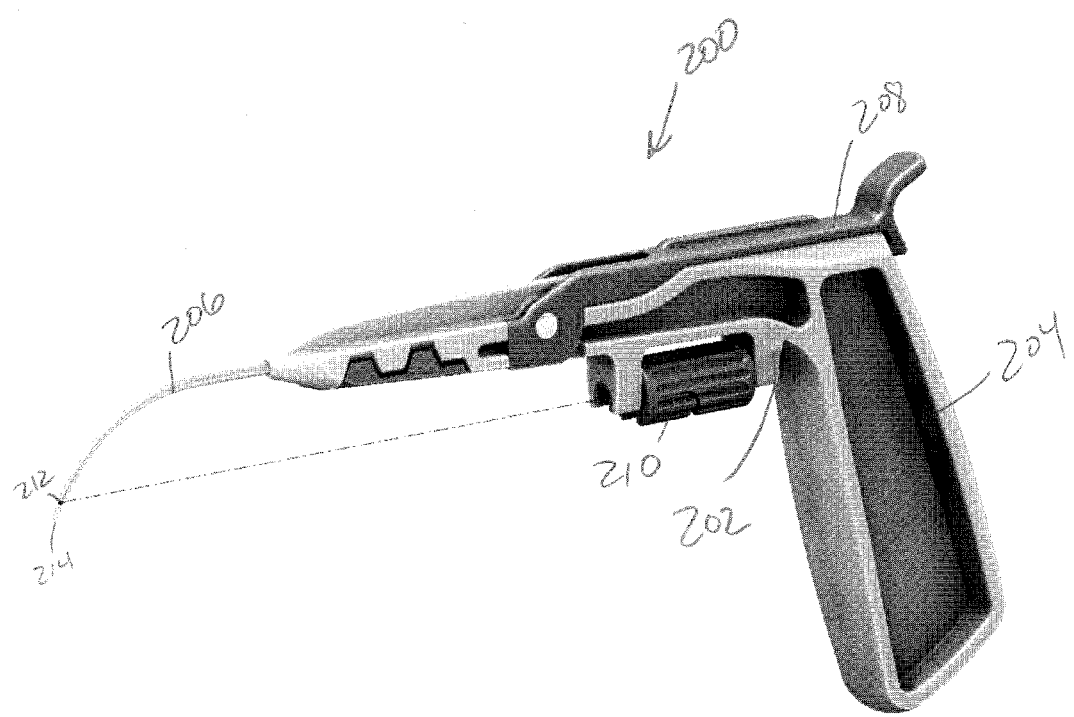
FIG. 31 is a side view of an example embodiment of a suture insertion device according to the present disclosure.
Figure 32:
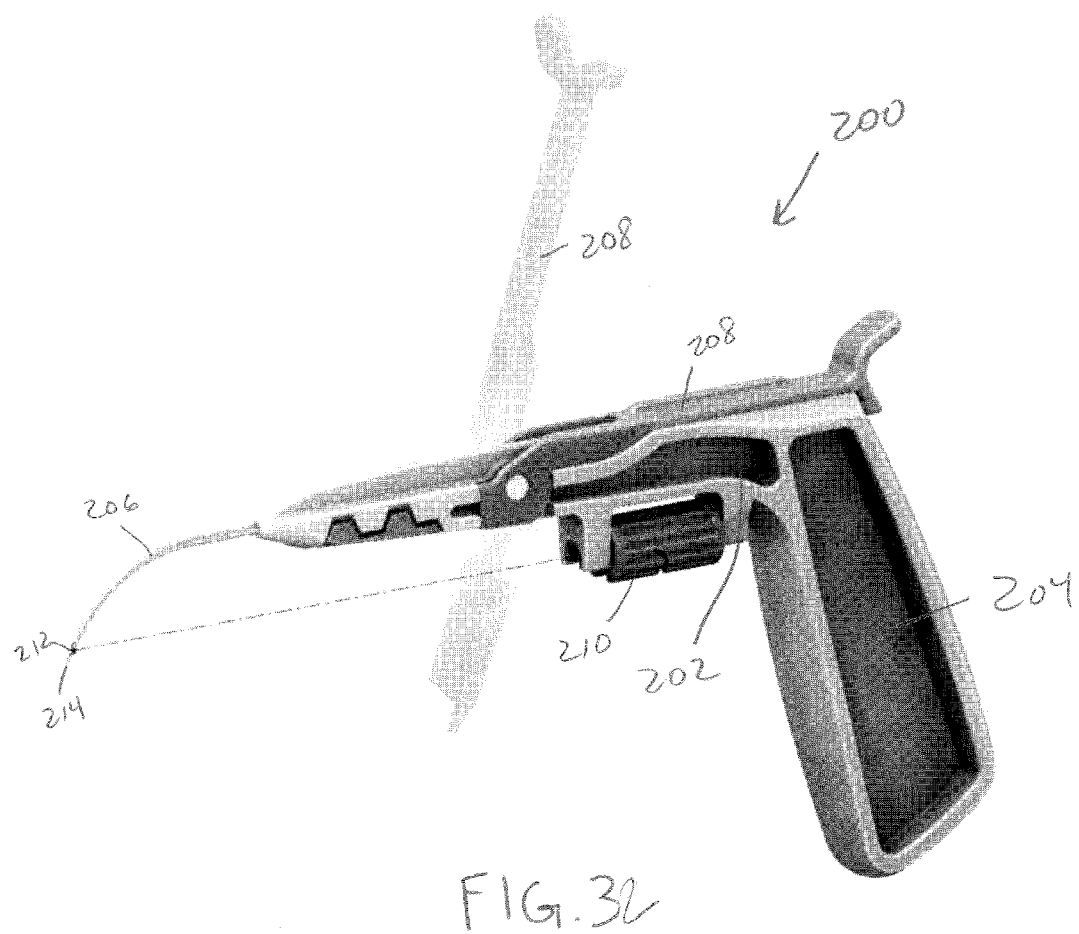
FIG. 32 is a side view of the device of FIG. 31.

FIGS. 31 and 32 illustrate yet another example embodiment of a suture insertion device 200 according to the present disclosure. In an example embodiment, suture insertion device 200 includes a main body 202, handle 204, a piercing shaft 206, a clamp 208, and a twisting device 210. Piercing shaft 206 includes a threading notch 212 and a piercing end 214 with a sharp tip that allows piercing shaft 206 to be inserted into a patient's soft palate 22. Because piecing end 214 pierces a patient's skin, suture insertion device 200 is preferably a disposable, single-use device that can be discarded after a single procedure so as not to spread infection amongst patients.

FIGS. 31 to 38 demonstrate an example method of using suture insertion device 200 to lift, suspend and stiffen a patient's soft palate and/or uvula to open the patient's airways. Preferably, suture insertion device 200 is not preloaded with a suture. Instead, suture insertion device can be loaded with any type of suture that a doctor chooses to best treat a specific patient.

Figure 33:
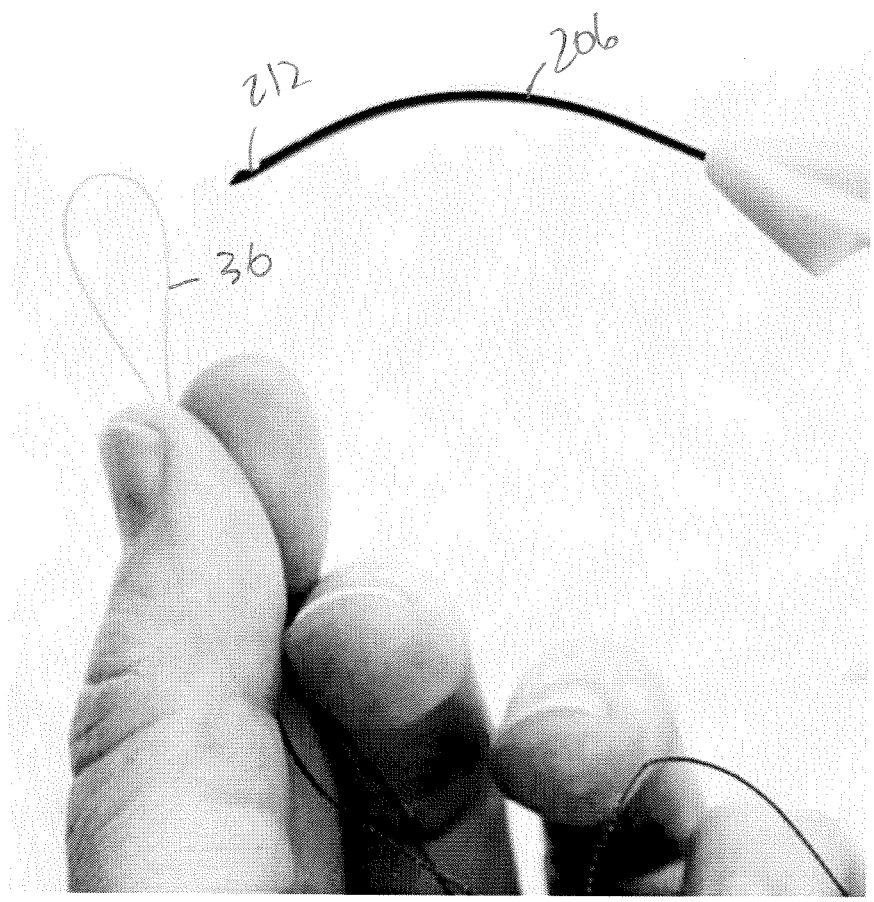
FIG. 33 is a side view illustrating a method of receiving a suture on the device of FIG. 31.

FIG. 31 shows suture insertion device 200 in a first, loading configuration. While the suture insertion device 200 is in the loading configuration, a suture 36 can be looped over threading notch 212, as shown in FIG. 33. In the illustrated embodiment, suture 36 remains outside of piercing shaft 206. Since the center portion of the suture 36 will be the first portion of the suture to contact and enter the patient's soft palate 22 and/or uvula 24, the center portion of the suture 36 is preferably clear (no barbs), which allows the center portion of the suture to be more easily inserted into the soft palate.

Figure 34:
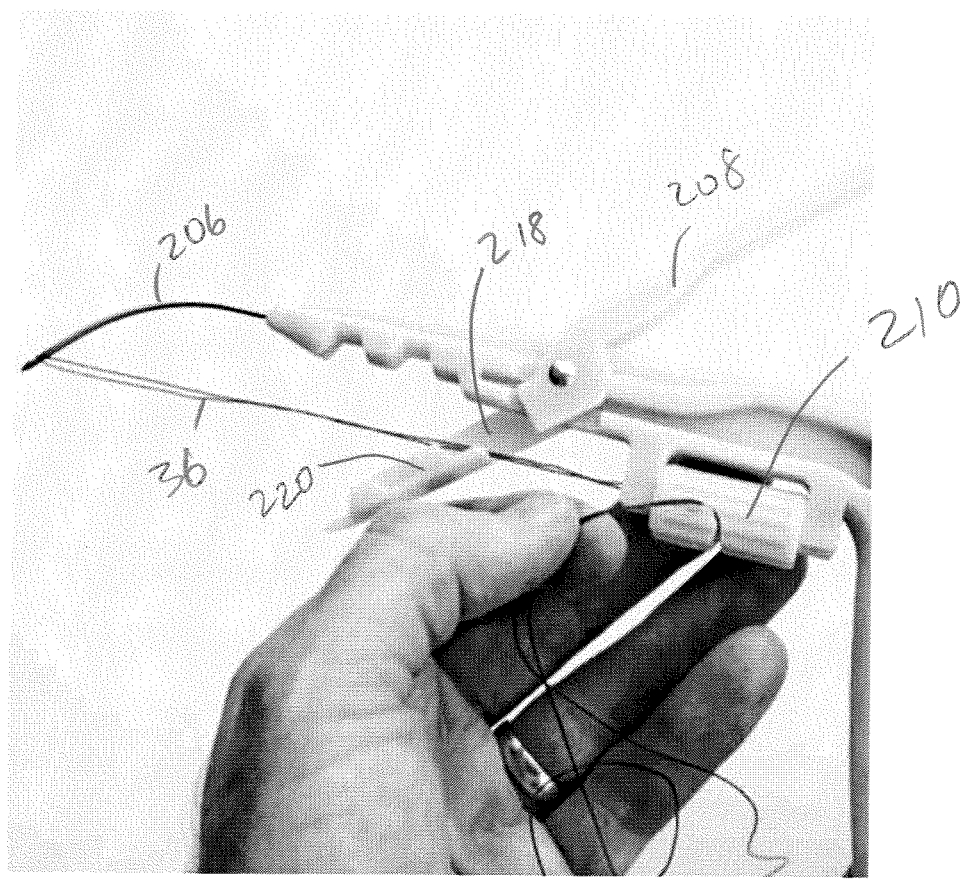
FIG. 34 is a side view illustrating a method of receiving a suture on the device of FIG. 31.
Figure 35:
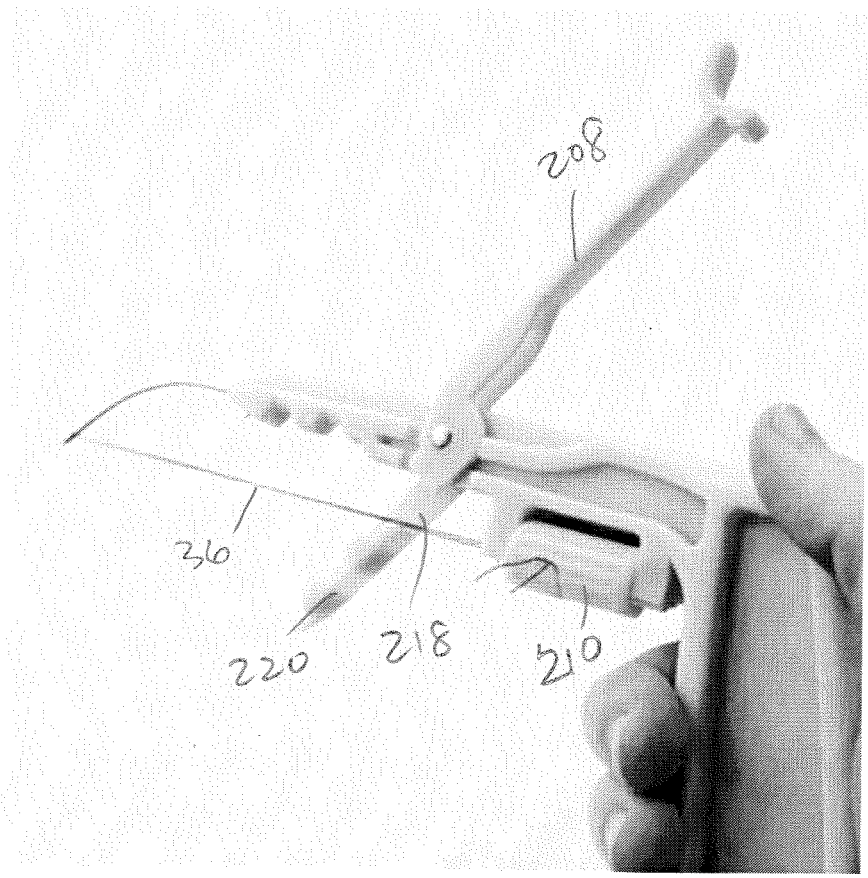
FIG. 35 is a side view illustrating a method of receiving a suture on the device of FIG. 31.
Figure 36:
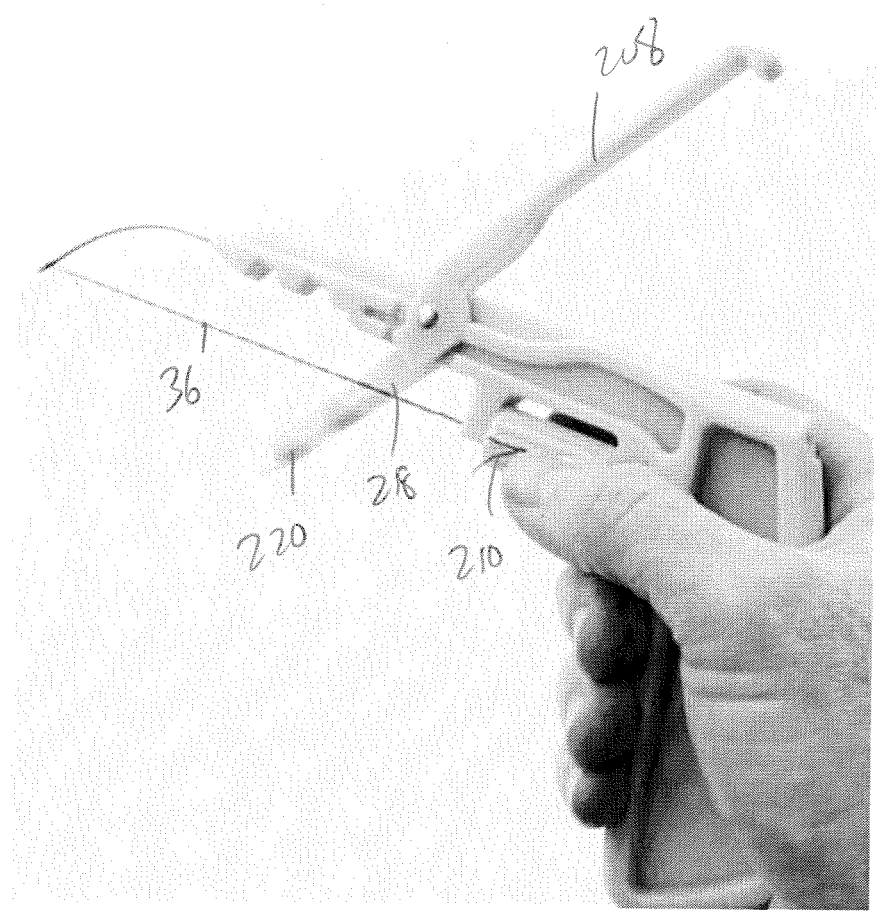
FIG. 36 is a side view illustrating a method of receiving a suture on the device of FIG. 31.

Referring now to FIG. 34, clamp 208 can be released to an open position so that after being looped over threading notch 212, suture 36 can be threaded through an aperture 218 in the bottom portion 220 of clamp 208 and pulled through twisting device 210. In an example embodiment, suture 36 can be substantially taught between threading notch 212 and twisting device 210. The doctor performing the procedure can adjust the suture 36 as needed. Once pulled through twisting device 210, suture 36 can be twisted by turning twisting device 210. In the illustrated embodiment, twisting device 210 is a twisting knob, but those of ordinary skill in the art will recognize other ways to twist suture 36 before insertion into a patient's soft palate 22 and/or uvula 24. Twisting suture 36 allows suture 36 to be more easily inserted into a patient's soft palate 22. Twisting suture 36 also creates barbs in multiple directions to grab the patient's soft palate, doubles the strength of the suture 36, and creates less slipping as the suture 36 pulls on the patient's soft palate 22 and/or uvula 24. Before twisting suture 36, the ends of suture 36 attached to twisting device 210 can be cut to prevent wrapping and binding as suture 36 is twisted. FIG. 35 illustrates suture insertion device 200 after suture 36 has been cut, and FIG. 36 illustrates suture insertion device 200 after the suture 36 has been twisted.

Figure 37:
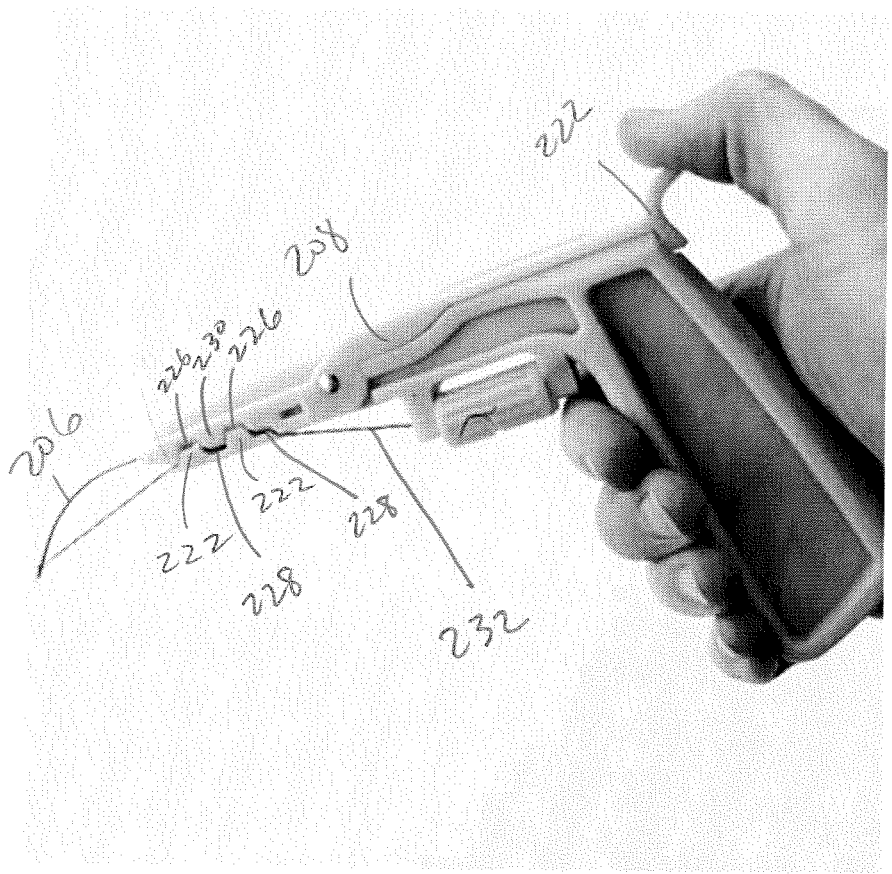
FIG. 37 is a side view illustrating a method of receiving a suture on the device of FIG. 31.

Once the suture 36 has been twisted, clamp 208 can be clamped to a closed position, as illustrated in FIG. 37, by pulling down on the upper portion 222 with a thumb. Clamping clamp 208 in the closed position pulls suture 36 closer to piercing shaft 206 for easier insertion into a patient's soft palate 22. Clamp 208 can include protrusions 224 that mate with apertures 226 in main body 202 and/or apertures 228 that mate with protrusions 230 in main body 202. Once clamped, suture 36 can be cut again at an intermediate portion 232 to release suture 36 from attachment to twisting device 210.

Figure 38:
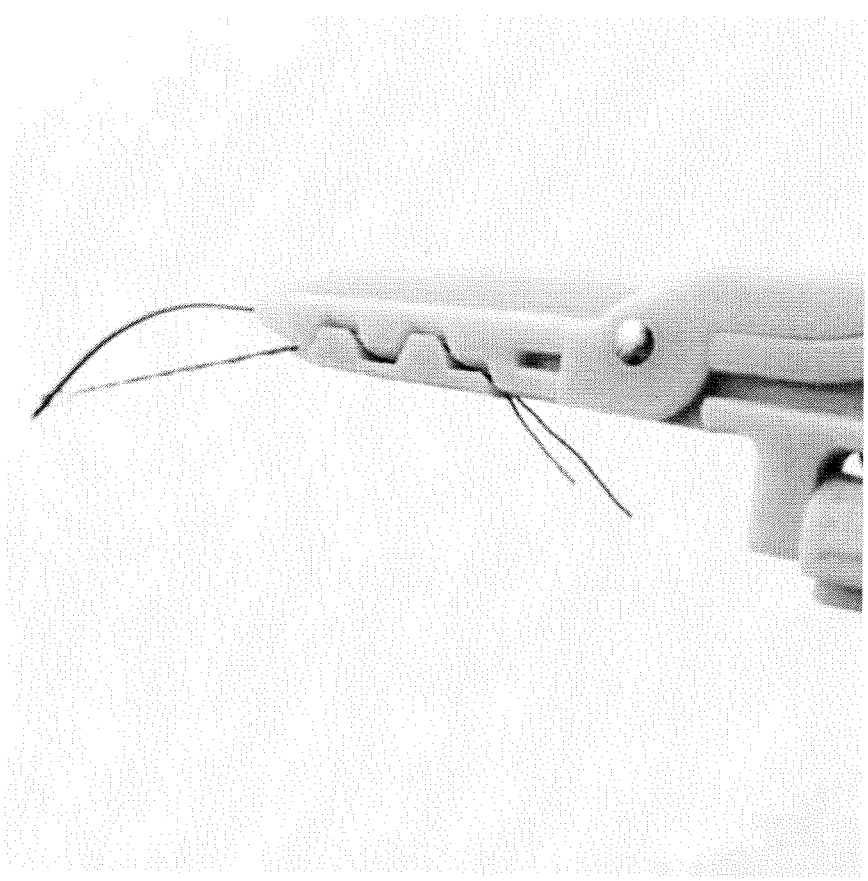
FIG. 38 is a side view illustrating a method of receiving a suture on the device of FIG. 31.

FIG. 38 shows a suture 36 ready for insertion into a patient's soft palate 22 and/or uvula 34 after being cut and released from twisting device 210. At this stage, piercing shaft 206 of suture insertion device 200 can be inserted into a patient's soft palate 22 at a high point at the midline of the soft palate 22. The placement of suture insertion device 200 should be verified. Piercing shaft 206 of suture insertion device 200 can be inserted into the soft palate 22 so that the piercing end 214 extends to almost the tip 29 of the patient's uvula 24. Piercing shaft 206 of suture insertion device 200 can also be inserted into the soft palate so that the piercing end 214 extends to different locations in the soft palate 22. The curve of piercing shaft 206 is designed to approximately match the curvature of the patient's soft palate 22. Piercing shaft 206 can optionally include depth markings so that the doctor performing the procedure can accurately determine how far the piercing shaft 206 has been inserted into the patient's soft palate. In an example embodiment, piercing shaft 206 includes an 18 mm straight portion and a curved portion with a 20 mm radius. In another example embodiment, piercing shaft 206 includes a 9 mm straight portion and a curved portion with a 27 mm radius. In another example embodiment, piercing shaft 206 includes a curved portion with a 38 mm radius. Those of ordinary skill in the art will understand that the length and curvature of piercing shaft 206 will vary according to the anatomic site.

Once the piercing shaft 206 has been inserted into the patient's soft palate 22, clamp 208 can again be released to the open position, which releases suture 36 from clamp 208 so that piercing shaft 206 can be withdrawn from the patient's soft palate 22 without withdrawing suture 36, the barbs 38 of which will grab the tissue in the patient's soft palate. Once piercing shaft 206 has been withdrawn from the patient's soft palate 22, the patient's soft palate 22 and/or uvula 24 can be lifted and stiffened by pulling the suture 36 in a direction different from the insertion direction of the piercing shaft 206. The pulling lifts the soft palate 22 and/or uvula 24 as the barbs of the suture 36 grab the patient's soft palate and/or uvula and pull the soft palate and/or uvula in the direction of the pulling. The pulling also stiffens the soft palate 22 and/or uvula 24 by compressing the soft palate and/or uvula into a smaller area. The barbs 38 suspend the soft palate 22 and/or uvula 24 in the lifted and stiffened position once the doctor has appropriately positioned the soft palate and/or uvula. Proper placement of the suture 36 can be verified by tugging and wiggling the suture. In an example embodiment, the center portion and/or another portion of suture 36 can include a sealing element so that the patient's soft palate 22 and/or uvula 24 will not be released over time. In one embodiment, the sealing element can be a tissue sealant to secure or fix the cut end of the suture and achieve long term lifting of the palate. In another embodiment, the sealing element can be a knot or clip to secure or fix the cut end of the suture and achieve long term lifting of the palate. In yet another example embodiment, the suture 36 can be inserted into the patient's soft palate 22 and uvula 24 using the triangular approach described above.

Figure 39:
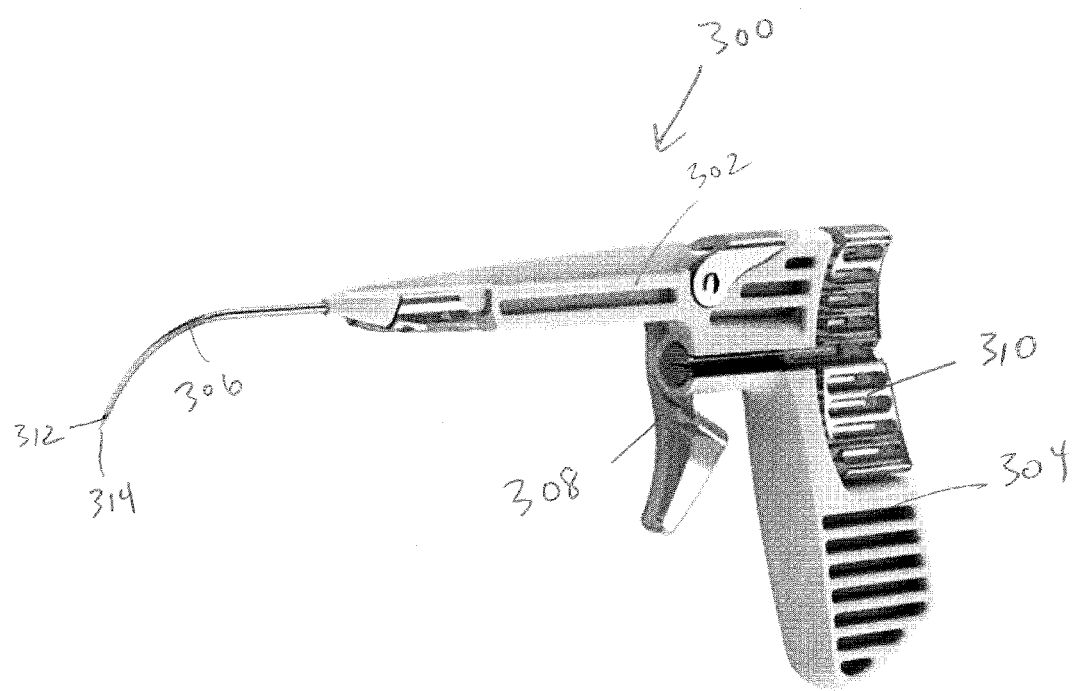
FIG. 39 is a side view of an example embodiment of a suture insertion device according to the present disclosure.

FIG. 39 illustrates yet another example embodiment of a suture insertion device 300 according to the present disclosure. In an example embodiment, suture insertion device 300 includes a main body 302, a handle 304, a piercing shaft 306, a clamp 308, and a twisting device 310. Piercing shaft 306 includes a threading notch 312 and a piercing end 314 with a sharp tip that allows piercing shaft 306 to be inserted into a patient's soft palate 22. Because piecing end 314 pierces a patient's skin, suture insertion device 300 is preferably a disposable, single-use device that can be discarded after a single procedure so as not to spread infection amongst patients.

Figure 40:
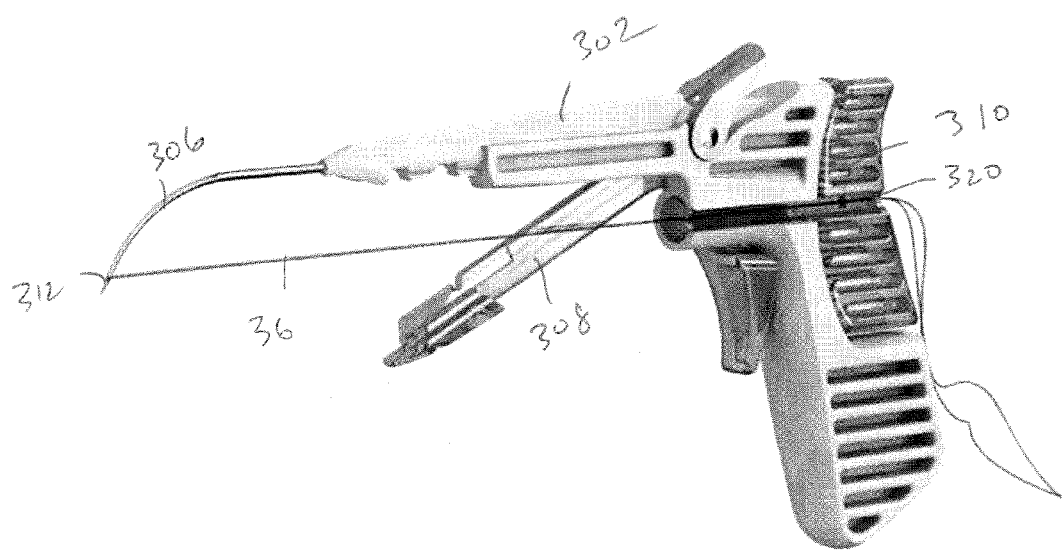
FIG. 40 is a side view illustrating a method of receiving a suture on the device of FIG. 39.
Figure 41:
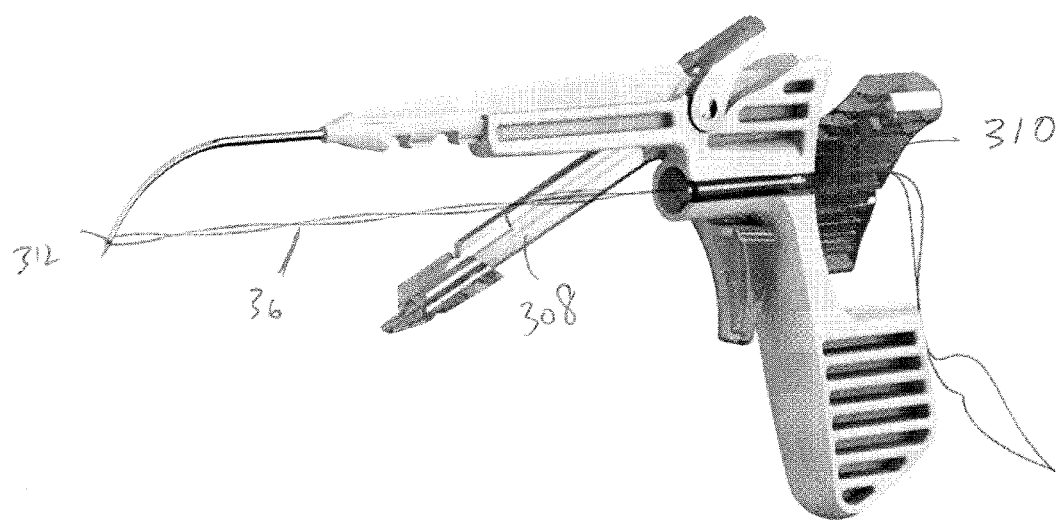
FIG. 41 is a side view illustrating a method of receiving a suture on the device of FIG. 39.
Figure 42:
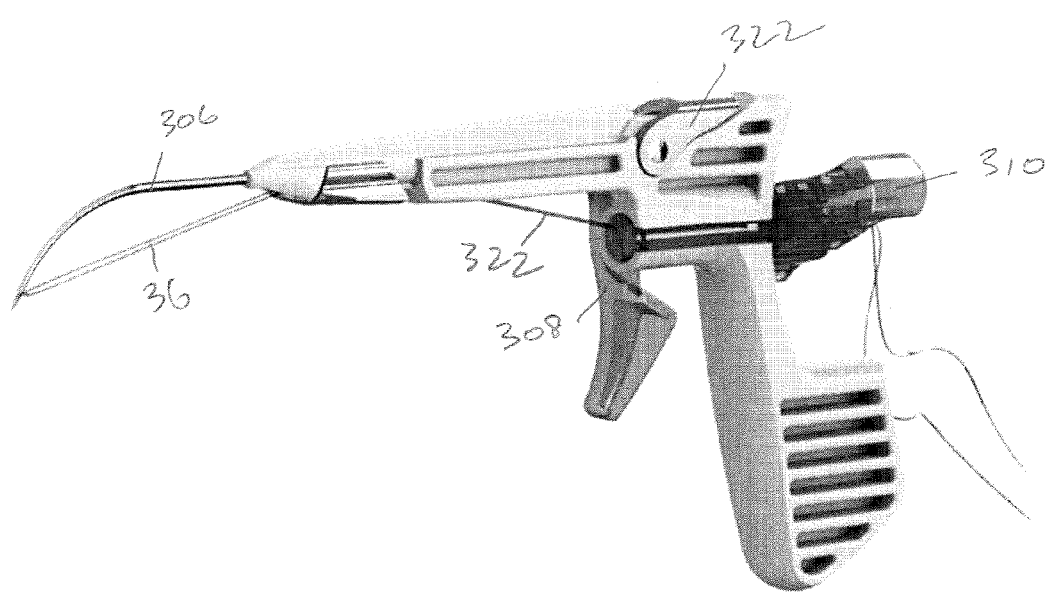
FIG. 42 is a side view illustrating a method of receiving a suture on the device of FIG. 39.

FIGS. 40 to 42 demonstrate an example method of using suture insertion device 300 to lift, suspend and stiffen a patient's soft palate and/or uvula to open the patient's airways. Preferably, suture insertion device 300 is not preloaded with a suture. Instead, suture insertion device 300 can be loaded with any type of suture that a doctor chooses to best treat a specific patient.

FIG. 40 shows suture insertion device 300 in a first, loading configuration. While the suture insertion device 300 is in the loading configuration, a suture 36 can be looped over threading notch 312. In the illustrated embodiment, suture 36 remains outside of piercing shaft 306. Since the center portion of the suture 36 will be the first portion of the suture to contact and enter the patient's soft palate 22 and/or uvula 24, the center portion of the suture 36 is preferably clear (no barbs), which allows the center portion of the suture to be more easily inserted into the soft palate.

In FIG. 40, clamp 308 is shown to be released to an open position so that after being looped over threading notch 312, suture 36 can be threaded between clamp 308 and main body 302 and pulled through a suture retaining element 320 in twisting device 310. In an example embodiment, suture 36 can be substantially taught between threading notch 312 and twisting device 310. The doctor performing the procedure can adjust the suture 36 as needed. Once pulled through twisting device 310, suture 36 can be twisted by turning twisting device 310, as shown in FIG. 41. Twisting suture 36 allows suture 36 to be more easily inserted into a patient's soft palate 22. Twisting suture 36 also creates barbs in multiple directions to grab the patient's soft palate, doubles the strength of the suture 36, and creates less slipping as the suture 36 pulls on the patient's soft palate 22 and/or uvula 24.

Once the suture 36 has been twisted, clamp 308 can be clamped to a closed position, as illustrated in FIG. 42, by pulling down on the upper portion 322 of clamp 308 with a thumb. Clamping clamp 308 in the closed position pulls suture 36 closer to piercing shaft 306 for easier insertion into a patient's soft palate 22. Clamp 308 can include protrusions that mate with apertures in main body 202 and/or apertures that mate with protrusions in main body 202. Once clamped, suture 36 can be cut again at an intermediate portion 322 to release suture 36 from attachment to twisting device 310.

FIG. 42 shows a suture 36 ready for insertion into a patient's soft palate 22 and/or uvula 34 after being cut and released from twisting device 310. At this stage, piercing shaft 306 of suture insertion device 300 can be inserted into a patient's soft palate 22 at a high point at the midline of the soft palate 22. The placement of suture insertion device 300 should be verified. Piercing shaft 306 of suture insertion device 300 can be inserted into the soft palate 22 so that the piercing end 314 extends to almost the tip 29 of the patient's uvula 24. Piercing shaft 306 of suture insertion device 200 can also be inserted into the soft palate so that the piercing end 314 extends to different locations in the soft palate 22. The curve of piercing shaft 306 is designed to approximately match the curvature of the patient's soft palate 22. Piercing shaft 306 can optionally include depth markings so that the doctor performing the procedure can accurately determine how far the piercing shaft 306 has been inserted into the patient's soft palate. In an example embodiment, piercing shaft 306 includes an 18 mm straight portion and a curved portion with a 20 mm radius. In another example embodiment, piercing shaft 306 includes a 9 mm straight portion and a curved portion with a 27 mm radius. In another example embodiment, piercing shaft 306 includes a curved portion with a 38 mm radius. Those of ordinary skill in the art will understand that the length and curvature of piercing shaft 306 will vary according to the anatomic site.

Once the piercing shaft 306 has been inserted into the patient's soft palate 22, clamp 308 can again be released to the open position, which releases suture 36 from clamp 308 so that piercing shaft 306 can be withdrawn from the patient's soft palate 22 without withdrawing suture 36, the barbs 38 of which will grab the tissue in the patient's soft palate. Once piercing shaft 306 has been withdrawn from the patient's soft palate 22, the patient's soft palate 22 and/or uvula 24 can be lifted, suspended and stiffened by pulling the suture 36 in a direction different from the insertion direction of the piercing shaft 306. The pulling lifts the soft palate 22 and/or uvula 24 as the barbs of the suture 36 grab the patient's soft palate and/or uvula and pull the soft palate and/or uvula in the direction of the pulling. The pulling also stiffens the soft palate 22 and/or uvula 24 by compressing the soft palate and/or uvula into a smaller area. The barbs 38 suspend the soft palate 22 and/or uvula 24 in the lifted and stiffened position once the doctor has appropriately positioned the soft palate and/or uvula. Proper placement of the suture 36 can be verified by tugging and wiggling the suture. In an example embodiment, the center portion and/or another portion of suture 36 can include a sealing element so that the patient's soft palate 22 and/or uvula 24 will not be released over time. In one embodiment, the sealing element can be a tissue sealant to secure or fix the cut end of the suture and achieve long term lifting of the palate. In another embodiment, the sealing element can be a knot or clip to secure or fix the cut end of the suture and achieve long term lifting of the palate. In yet another example embodiment, the suture 36 can be inserted into the patient's soft palate 22 and uvula 24 using the triangular approach described above.

The methods and apparatuses disclosed herein are advantageous because they preserve the native palate anatomy and its function. The uvula lubricates and sweeps the posterior pharyngeal wall during swallowing and clears it from stagnant secretions. By simply lifting, suspending and stiffening the soft palate and/or uvula, instead of trimming the soft palate and/or uvula, the disclosed methods and apparatuses do not affect the function of the uvula, only the shape of the uvula. In an example embodiment, the methods and apparatuses disclosed herein can turn a low frequency-high amplitude (Velum Type) snoring from an elongated uvula into a high frequency-low amplitude sound.

Modifications in addition to those described above may be made to the structures and techniques described herein without departing from the spirit and scope of the disclosure. Accordingly, although specific embodiments have been described, these are examples only and are not limiting on the scope of the disclosure.

EXAMPLES

The following non-limiting examples present evidence supporting the effectiveness of the methods and apparatuses described herein. Specifically, these examples show that the methods and apparatuses described herein are effective to lift, suspend and stiffen a patient's tissue, more specifically a patient's soft palate.

Example 1

Patient 1

In a first example, Patient 1 was an adult male. Size 0 barbed sutures were inserted into Patient 1's soft palate using a needle. The sutures were inserted into Patient 1's soft palate using both the straight down-and-up approach and triangular approach described above. The lengths of the test sutures were approximately the length of the patient's palate. With both approaches it was observed that the sutures effectively lifted, suspended and stiffened Patient 1's soft palate and uvula. The sutures were removed from Patient 1 after the test was complete.

Example 2

Patient 2

In a second example, Patient 2 was an adult male. Size 1 barbed sutures were inserted into Patient 2's soft palate using a needle. The sutures were inserted into Patient 2's soft palate using both the straight down-and-up approach and triangular approach described above. The lengths of the test sutures were approximately the length of the patient's palate. With both approaches it was observed that the sutures effectively lifted, suspended and stiffened Patient 2's soft palate and uvula. The sutures were removed from Patient 2 after the test was complete.

Example 3

Patient 3

In a third example, Patient 3 was an adult female. Size 2 barbed sutures were inserted into Patient 3's soft palate using a needle. The sutures were inserted into Patient 3's soft palate using both the straight down-and-up approach and triangular approach described above. The lengths of the test sutures were approximately the length of the patient's palate. With both approaches it was observed that the sutures effectively lifted, suspended and stiffened Patient 3's soft palate and uvula. The sutures were removed from Patient 3 after the test was complete.

Example 4

Meat

In a fourth example, a suture insertion device according to the present disclosure was tested on several samples of meat to determine the effectiveness of the device in lifting and suspending with a single suture. 15 gram, 30 gram and 150 gram meat samples were tested to determine whether a single suture inserted with the suture insertion device using the straight down-and-up approach described above could effectively lift and suspend the samples. These samples were chosen because they were heavier than a typical patient's soft palate and uvula.

The samples were first tested with a non-barbed size 0 nylon suture using the straight down-and-up approach described above. The non-barbed size 0 nylon sutures could not lift and suspend the samples of meat. Instead, the non-barbed size 0 nylon sutures were immediately pulled out of the samples.

The 15 gram, 30 gram and 150 gram meat samples were then tested with a barbed size 2 suture using the straight down-and-up approach described above. It was observed that using the suture insertion device with the barbed size 2 suture effectively lifted, suspended and stiffened each of the samples for at least 5 minutes until the test was concluded.

Additional Aspects of the Present Disclosure

Aspects of the subject matter described herein may be useful alone or in combination with any one or more of the other aspect described herein. Without limiting the foregoing description, in a first aspect of the present disclosure, a method of lifting and stiffening a patient's tissue includes inserting at least one suture into the patient's tissue in a first direction, pulling the suture in a second direction so as to lift and suspend the tissue in a lifted position and stiffen the tissue in the lifted position, and cutting the suture so that the tissue remains in the lifted position.

In accordance with a second aspect of the present disclosure, which may be used in combination with any other aspect or combination of aspects listed herein, the patient's tissue is the patient's soft palate.

In accordance with a third aspect of the present disclosure, which may be used in combination with any other aspect or combination of aspects listed herein, inserting the at least one suture into the patient's soft palate includes inserting the at least one suture proximal to a midline patient's soft palate.

In accordance with a fourth aspect of the present disclosure, which may be used in combination with any other aspect or combination of aspects listed herein, inserting the at least one suture into the patient's soft palate includes inserting the at least one suture into the patient's soft palate and uvula.

In accordance with a fifth aspect of the present disclosure, which may be used in combination with any other aspect or combination of aspects listed herein, pulling the suture includes lifting, suspending and stiffening the patient's uvula.

In accordance with a sixth aspect of the present disclosure, which may be used in combination with any other aspect or combination of aspects listed herein, the method includes enabling the suture to dissolve in the patient's soft palate.

In accordance with a seventh aspect of the present disclosure, which may be used in combination with any other aspect or combination of aspects listed herein, the method includes anesthetizing the patient's soft palate.

In accordance with an eighth aspect of the present disclosure, which may be used in combination with any other aspect or combination of aspects listed herein, inserting the at least one suture into the patient's soft palate includes inserting the at least one suture with a needle.

In accordance with a ninth aspect of the present disclosure, which may be used in combination with any other aspect or combination of aspects listed herein, inserting the at least one suture into the patient's soft palate includes inserting the at least one suture with a suture insertion device, and further including releasing the suture continuously from the suture insertion device.

In accordance with a tenth aspect of the present disclosure, which may be used in combination with any other aspect or combination of aspects listed herein, inserting the at least one suture into the patient's soft palate includes inserting the at least one suture with a suture insertion device, and further including releasing the suture from the suture insertion device in discrete increments.

In accordance with an eleventh aspect of the present disclosure, which may be used in combination with any other aspect or combination of aspects listed herein, a method of lifting and stiffening a patient's tissue includes loading a suture onto a piercing shaft of a suture insertion device, inserting the piercing shaft into the patient's tissue in a first direction, releasing the suture from the piercing shaft, withdrawing the piercing shaft from the patient's tissue, and pulling the suture in a second direction so as to lift, suspend and stiffen the tissue.

In accordance with a twelfth aspect of the present disclosure, which may be used in combination with any other aspect or combination of aspects listed herein, inserting the piercing shaft into the patient's tissue includes inserting the piercing shaft into the patient's soft palate.

In accordance with a thirteenth aspect of the present disclosure, which may be used in combination with any other aspect or combination of aspects listed herein, loading the suture onto the piercing shaft includes threading the suture through a threading notch in the piercing shaft.

In accordance with a fourteenth aspect of the present disclosure, which may be used in combination with any other aspect or combination of aspects listed herein, loading the suture onto the piercing shaft includes clamping the suture to the suture insertion device.

In accordance with a fifteenth aspect of the present disclosure, which may be used in combination with any other aspect or combination of aspects listed herein, releasing the suture from the piercing shaft includes unclamping the suture.

In accordance with a sixteenth aspect of the present disclosure, which may be used in combination with any other aspect or combination of aspects listed herein, loading the suture onto the piercing shaft includes twisting the suture.

In accordance with a seventh aspect of the present disclosure, which may be used in combination with any other aspect or combination of aspects listed herein, loading the suture onto the piercing shaft includes attaching the suture to an insertion shaft within the piercing shaft.

In accordance with a eighteenth aspect of the present disclosure, which may be used in combination with any other aspect or combination of aspects listed herein, loading the suture onto the piecing shaft includes pulling the suture through a first portion of the piecing shaft.

In accordance with a nineteenth aspect of the present disclosure, which may be used in combination with any other aspect or combination of aspects listed herein, releasing the suture from the piercing shaft includes pushing the suture through a second portion of the piercing shaft.

In accordance with a twentieth aspect of the present disclosure, which may be used in combination with any other aspect or combination of aspects listed herein, inserting the piercing shaft into the patient's soft palate includes inserting a piercing end of the piercing shaft so that the piercing end extends to almost a tip of a uvula.

In accordance with a twenty-first aspect of the present disclosure, which may be used in combination with any other aspect or combination of aspects listed herein, the method includes applying a sealing element to the suture.

In accordance with a twenty-second aspect of the present disclosure, which may be used in combination with any other aspect or combination of aspects listed herein, a suture insertion device includes a body, and a piercing shaft connected to the body, the piercing shaft including a piercing end, the piercing shaft configured to pierce a patient's tissue with the piercing end and insert a suture into the patient's tissue in a first direction, wherein the piercing shaft is further configured to release the suture into the patient's tissue such that the suture can be pulled in a second direction to lift, suspend and stiffen the patient's tissue once the piercing shaft is removed from the patient's tissue.

In accordance with a twenty-third aspect of the present disclosure, which may be used in combination with any other aspect or combination of aspects listed herein, the patient's tissue is the patient's soft palate.

In accordance with a twenty-fourth aspect of the present disclosure, which may be used in combination with any other aspect or combination of aspects listed herein, the piercing shaft is a cannula.

In accordance with a twenty-fifth aspect of the present disclosure, which may be used in combination with any other aspect or combination of aspects listed herein, the piercing shaft includes a threading notch to receive the suture.

In accordance with a twenty-sixth aspect of the present disclosure, which may be used in combination with any other aspect or combination of aspects listed herein, the threading notch is located proximal to the piercing end.

In accordance with a twenty-seventh aspect of the present disclosure, which may be used in combination with any other aspect or combination of aspects listed herein, the threading notch is located distal to the piercing end.

In accordance with a twenty-eighth aspect of the present disclosure, which may be used in combination with any other aspect or combination of aspects listed herein, the suture insertion device includes an insertion shaft, the insertion shaft configured to release the suture from the piercing shaft.

In accordance with a twenty-ninth aspect of the present disclosure, which may be used in combination with any other aspect or combination of aspects listed herein, the threading notch is located distal to the piercing end and the insertion shaft pulls the suture through the piercing shaft.

In accordance with a thirtieth aspect of the present disclosure, which may be used in combination with any other aspect or combination of aspects listed herein, the threading notch is located proximal to the piercing end and the insertion shaft pushes the suture off of the piercing shaft.

In accordance with a thirty-first aspect of the present disclosure, which may be used in combination with any other aspect or combination of aspects listed herein, the suture insertion device includes a clamp configure to clamp the suture to the body for prior to the piercing shaft being inserted into the patient's tissue and release the suture from the body after the piercing shaft is inserted into the patient's tissue.

In accordance with a thirty-second aspect of the present disclosure, which may be used in combination with any other aspect or combination of aspects listed herein, the suture insertion device includes a twisting device.

In accordance with a thirty-third aspect of the present disclosure, which may be used in combination with any other aspect or combination of aspects listed herein, the suture insertion device includes a suture cutting device.

In accordance with a thirty-fourth aspect of the present disclosure, which may be used in combination with any other aspect or combination of aspects listed herein, the piercing shaft is curved to match the curvature of the patient's soft palate.

In accordance with a thirty-fifth aspect of the present disclosure, which may be used in combination with any other aspect or combination of aspects listed herein, the piercing shaft includes depth markings.

In accordance with a thirty-sixth aspect of the present disclosure, which may be used in combination with any other aspect or combination of aspects listed herein, the piercing shaft includes at least one suture-retaining groove.

In accordance with a thirty-seventh aspect of the present disclosure, which may be used in combination with any other aspect or combination of aspects listed herein, a suture insertion device includes a means for loading a suture, a means for inserting the suture into a patient's tissue in a first direction, and a means for releasing the suture so that the suture can be pulled in a second direction different from the first direction so as to lift, suspend and stiffen the tissue.

In accordance with a thirty-eighth aspect of the present disclosure, which may be used in combination with any other aspect or combination of aspects listed herein, the patient's tissue is the patient's soft palate.

In accordance with a thirty-ninth aspect of the present disclosure, which may be used in combination with any other aspect or combination of aspects listed herein, the suture insertion device includes a cannula, wherein the means for loading the suture includes a means for pulling the suture through the cannula.

In accordance with a fortieth aspect of the present disclosure, which may be used in combination with any other aspect or combination of aspects listed herein, the means for loading the suture includes a means for clamping the suture.

In accordance with a forty-first aspect of the present disclosure, which may be used in combination with any other aspect or combination of aspects listed herein, the means for loading the suture includes a means for twisting the suture.

In accordance with a forty-second aspect of the present disclosure, which may be used in combination with any other aspect or combination of aspects listed herein, the suture insertion device includes a means for determining how deep the suture has been inserted into the patient's tissue.

In accordance with a forty-third aspect of the present disclosure, which may be used in combination with any other aspect or combination of aspects listed herein, a suture insertion device includes a body, a piercing shaft connected to the body, the piercing shaft including a cannula and a threading notch configured to receive a suture, and an insertion shaft moveable within the cannula, the insertion shaft configured to release the suture from the piercing shaft.

In accordance with a forty-fourth aspect of the present disclosure, which may be used in combination with any other aspect or combination of aspects listed herein, the patient's tissue is the patient's soft palate.

In accordance with a forty-fifth aspect of the present disclosure, which may be used in combination with any other aspect or combination of aspects listed herein, the threading notch is located proximal to the piercing end.

In accordance with a forty-sixth aspect of the present disclosure, which may be used in combination with any other aspect or combination of aspects listed herein, the threading notch is located distal to the piercing end.

In accordance with a forty-seventh aspect of the present disclosure, which may be used in combination with any other aspect or combination of aspects listed herein, the insertion shaft pulls the suture through the piercing shaft.

In accordance with a forty-eighth aspect of the present disclosure, which may be used in combination with any other aspect or combination of aspects listed herein, the insertion shaft pushes the suture off of the piercing shaft.

In accordance with a forty-ninth aspect of the present disclosure, which may be used in combination with any other aspect or combination of aspects listed herein, the piercing shaft includes at least one suture-retaining groove.

In accordance with a fiftieth aspect of the present disclosure, which may be used in combination with any other aspect or combination of aspects listed herein, a suture insertion device includes a body, a piercing shaft connected to the body, the piercing shaft including a threading notch configured to receive a suture, and a clamp configured to clamp the suture to the body when the piercing shaft is inserted into a patient's tissue and to release the suture from the body when the piercing shaft is withdrawn from the patient's tissue.

In accordance with a fifty-first aspect of the present disclosure, which may be used in combination with any other aspect or combination of aspects listed herein, the patient's tissue is the patient's soft palate.

In accordance with a fifty-second aspect of the present disclosure, which may be used in combination with any other aspect or combination of aspects listed herein, the suture insertion device includes a twisting device.

In accordance with a fifty-third aspect of the present disclosure, which may be used in combination with any other aspect or combination of aspects listed herein, the suture can be threaded through an aperture in the clamp and pulled through the twisting device.

In accordance with a fifty-fourth aspect of the present disclosure, which may be used in combination with any other aspect or combination of aspects listed herein, the clamp includes protrusions that mate with apertures in the body.

In accordance with a fifty-fifth aspect of the present disclosure, which may be used in combination with any other aspect or combination of aspects listed herein, the clamp includes apertures that mate with protrusions in the body.

In accordance with a fifty-sixth aspect of the present disclosure, which may be used in combination with any other aspect or combination of aspects listed herein, the clamp is operable between an open position and a closed position.

In accordance with a fifty-seventh aspect of the present disclosure, which may be used in combination with any other aspect or combination of aspects listed herein, the suture insertion device includes a suture cutting device.

In accordance with a fifty-eighth aspect of the present disclosure, which may be used in combination with any other aspect or combination of aspects listed herein, the piercing shaft is curved to match the curvature of the patient's soft palate.

In accordance with a fifty-ninth aspect of the present disclosure, which may be used in combination with any other aspect or combination of aspects listed herein, the piercing shaft includes depth markings.

In accordance with a sixtieth aspect of the present disclosure, which may be used in combination with any other aspect or combination of aspects listed herein, the piercing shaft includes at least one suture-retaining groove.

The invention is claimed as follows:

1. A method of lifting and stiffening a patient's tissue, comprising:
   loading a suture into a notch on a notched portion of an outer surface of a shaft;
   after loading the suture, inserting the notched portion of the loaded shaft into the patient's tissue in a first direction at an insertion point in the patient's tissue;
   after inserting the notched shaft, releasing the suture from the notch on the outer surface of the shaft without cutting the suture;
   withdrawing the noticed portion of the shaft from the patient's tissue at the insertion point, leaving the suture at least partially in the tissue such that the suture only protrudes from the tissue at the insertion point after the shaft is withdrawn;
   pulling the suture in a second direction so as to lift and suspend the tissue in a lifted position and stiffen the tissue in the lifted position; and
   cutting the suture so that the tissue remains in the lifted position.

2. The method of claim 1, wherein the patient's tissue is the patient's soft palate.

3. The method of claim 2, wherein inserting the loaded shaft into the patient's soft palate includes inserting the loaded shaft proximal to a midline of the patient's soft palate.

4. The method of claim 2, wherein inserting the loaded shaft into the patient's soft palate includes inserting the loaded shaft into the patient's soft palate and uvula.

5. The method of claim 4, wherein pulling the suture includes lifting, suspending and stiffening the patient's uvula.

6. The method of claim 2, further including enabling the suture to dissolve in the patient's soft palate.

7. The method of claim 2, wherein inserting the loaded shaft into the patient's soft palate includes inserting the loaded shaft of a needle.

8. The method of claim 2, wherein inserting the loaded shaft into the patient's soft palate includes inserting the loaded shaft with a suture insertion device, and further including releasing the suture continuously from the suture insertion device.

9. The method of claim 1, wherein the suture includes bidirectional barbs.

10. The method of claim 1, wherein the notch is located on a curved piercing end of the shaft.

11. The method of claim 1, wherein loading the suture into the notch on the outer surface of the shaft includes looping the suture over the notch such that the suture remains outside of the shaft.

12. The method of claim 1, wherein inserting the loaded shaft into the patient's tissue in a first direction includes piercing the patient's tissue with the loaded shaft.

13. The method of claim 1, wherein the shaft includes a suture retaining groove in the outer surface that prevents barbs of the suture from grabbing the patient's tissue as the shaft is inserted into the patient's tissue.

* * * * *